United States Patent
Tang et al.

(10) Patent No.: US 11,816,832 B2
(45) Date of Patent: Nov. 14, 2023

(54) DEVICES, SYSTEMS, AND METHODS FOR MEDICAL IMAGING

(71) Applicant: CANON MEDICAL SYSTEMS CORPORATION, Tochigi (JP)

(72) Inventors: Qiulin Tang, Buffalo Grove, IL (US); Jian Zhou, Buffalo Grove, IL (US); Zhou Yu, Glenview, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 301 days.

(21) Appl. No.: 16/951,931

(22) Filed: Nov. 18, 2020

(65) Prior Publication Data

US 2022/0156919 A1 May 19, 2022

(51) Int. Cl.
*G06T 7/00* (2017.01)
*G16H 30/40* (2018.01)
(Continued)

(52) U.S. Cl.
CPC ............ *G06T 7/0012* (2013.01); *A61B 6/032* (2013.01); *A61B 6/504* (2013.01); *A61B 6/5264* (2013.01); *G06N 3/08* (2013.01); *G06T 7/12* (2017.01); *G06T 11/005* (2013.01); *G16H 30/40* (2018.01); *G16H 50/20* (2018.01); *G16H 50/50* (2018.01);
(Continued)

(58) Field of Classification Search
CPC . G06T 7/0012; G06T 11/005; G06T 2211/40; G16H 70/00; G06N 3/02
See application file for complete search history.

(56) References Cited

U.S. PATENT DOCUMENTS 8,600,132 B2 12/2013 Razifar
8,611,630 B1 * 12/2013 Katsevich ............. G06T 7/0012
382/131
(Continued)

OTHER PUBLICATIONS

Joscha Maier et al., Coronary Artery Motion Compensation for Short-Scan Cardiac CT Using a Spatial Transformer Network, The 6th International Conference on Image Formation in X-Ray Computed Tomography, Aug. 6, 2020.
(Continued)

*Primary Examiner* — John Villecco
*Assistant Examiner* — Courtney Joan Nelson
(74) *Attorney, Agent, or Firm* — Canon U.S.A., Inc. IP Division

(57) ABSTRACT

Devices, systems, and methods obtain scan data that were generated by scanning a scanned region, wherein the scan data include groups of scan data that were captured at respective angles; generate partial reconstructions of at least a part of the scanned region, wherein each partial reconstruction of the partial reconstructions is generated based on a respective one or more groups of the groups of scan data, and wherein a collective scanning range of the respective one or more groups is less than the angular scanning range; input the partial reconstructions into a machine-learning model, which generates one or more motion-compensated reconstructions of the at least part of the scanned region based on the partial reconstructions; calculate a respective edge entropy of each of the one or more motion-compensated reconstructions of the at least part of the scanned region; and adjust the machine-learning model based on the respective edge entropies.

20 Claims, 20 Drawing Sheets

(51) Int. Cl.
  G16H 50/20    (2018.01)
  G16H 50/70    (2018.01)
  G06N 3/08     (2023.01)
  G06T 7/12     (2017.01)
  G06T 11/00    (2006.01)
  A61B 6/03     (2006.01)
  A61B 6/00     (2006.01)
  G16H 50/50    (2018.01)

(52) U.S. Cl.
  CPC ... *G16H 50/70* (2018.01); *G06T 2207/10081* (2013.01); *G06T 2207/20081* (2013.01); *G06T 2207/20084* (2013.01); *G06T 2207/30101* (2013.01); *G06T 2211/436* (2013.01)

(56) References Cited

U.S. PATENT DOCUMENTS

| | | | |
|---|---|---|---|
| 9,189,851 | B2 | 11/2015 | Liao |
| 9,576,357 | B2 | 2/2017 | Averikou |
| 9,799,100 | B2 | 10/2017 | Guo |
| 2011/0142313 | A1* | 6/2011 | Pack ............... G06T 7/246 378/4 |
| 2019/0108441 | A1* | 4/2019 | Thibault ............. G06T 11/003 |
| 2019/0108904 | A1* | 4/2019 | Zhou ................ G06K 9/6298 |
| 2019/0353741 | A1 | 11/2019 | Bolster, Jr. |
| 2020/0118308 | A1 | 4/2020 | Nakanishi |
| 2020/0118669 | A1 | 4/2020 | Mohr |

OTHER PUBLICATIONS

Qiulin Tang et al., A fully four-dimensional, iterative motion estimation and compensation method for cardiac CT, Jun. 25, 2012.

A. Sisniega et al., Local Motion Estimation for Improved Cone-Beam CT Deformable Motion Compensation, The 6th International Conference on Image Formation in X-Ray Computed Tomography, Aug. 6, 2020.

Guotao Quan et al., Cardiac Motion Correction of Computed Tomography (CT) with Spatial Transformer Network, The 6th International Conference on Image Formation in X-Ray Computed Tomography, Aug. 6, 2020.

Alexander Katsevich et al., A Motion Estimation and Compensation Algorithm for 4D CBCT with Cyclic Deformation Model, The 6th International Conference on Image Formation in X-Ray Computed Tomography, Aug. 6, 2020.

Markus Susenburger et al., 4D Segmentation-Based Anatomy-Constrained Motion-Compensated Reconstruction of On-Board 4D CBCT Scans, The 6th International Conference on Image Formation in X-Ray Computed Tomography, Aug. 6, 2020.

Matt D. Holbrook et al., Deep Learning Based Distortion Correction and Material Decomposition for Photon Counting CT: A Simulation Study, The 6th International Conference on Image Formation in X-Ray Computed Tomography, Aug. 6, 2020.

Igor Peterlik et al., Motion Resilient Iterative 3D CBCT Reconstruction Based on Gradient Weighting, The 6th International Conference on Image Formation in X-Ray Computed Tomography, Aug. 6, 2020.

* cited by examiner

DEVICES, SYSTEMS, AND METHODS FOR MEDICAL IMAGING

BACKGROUND

Technical Field

This application generally concerns medical imaging.

Background

Medical imaging can produce images of the internal members of a patient's body. For example, computed tomography (CT) scans use multiple x-ray images of an object, which were taken from different angles, to generate an image of the interior of the object. Other medical-imaging modalities include, for example, X-ray radiography, ultrasonography, magnetic-resonance imaging (MRI), and positron emission tomography (PET). Once the images have been produced, a physician can use the images to diagnose a patient's injuries or diseases.

SUMMARY

Some embodiments of a method comprise obtaining scan data that were generated by scanning a scanned region, wherein the scan data include groups of scan data that were captured at respective angles, and wherein the respective angles of the groups of scan data collectively define an angular scanning range; generating partial reconstructions of at least a part of the scanned region, wherein each partial reconstruction of the partial reconstructions is generated based on a respective one or more groups of the groups of scan data, and wherein a collective scanning range of the respective one or more groups is less than the angular scanning range; inputting the partial reconstructions into a machine-learning model, which generates one or more motion-compensated reconstructions of the at least part of the scanned region based on the partial reconstructions; calculating a respective edge entropy of each of the one or more motion-compensated reconstructions of the at least part of the scanned region; and adjusting the machine-learning model based on the respective edge entropies.

Some embodiments of a system comprise one or more processors and one or more computer-readable storage media in communication with the one or more processors. The one or more processors and the one or more computer-readable media cooperate to perform operations that include obtaining scan data that were generated by scanning a scanned region, wherein the scan data include groups of scan data that were captured at respective angles, and wherein the respective angles of the groups of scan data collectively define an angular scanning range; generating an initial reconstruction of at least a part of the scanned region based on at least some of the groups of scan data; defining one or more patches in the at least a part of the scanned region based on the initial reconstruction; generating respective motion-corrected reconstructions of the one or more patches, wherein generating the respective motion-corrected reconstruction of a patch includes inputting scan data in the groups of scan data that correspond to the patch into a machine-learning model; and generating a motion-corrected reconstruction of the at least part of the scanned region based on the motion-corrected reconstructions of the one or more patches.

Some embodiments of one or more computer-readable storage media storing instructions that, when executed by one or more computing devices, cause the one or more computing devices to perform operations that comprise obtaining scan data that were generated by scanning a scanned region, wherein the scan data include groups of scan data that were captured at respective angles; generating partial reconstructions of at least a part of the scanned region, wherein each partial reconstruction of the partial reconstructions is generated based on a respective one or more groups of the groups of scan data; inputting the partial reconstructions into a machine-learning model, which generates one or more motion-compensated reconstructions of the at least part of the scanned region based on the partial reconstructions; calculating a respective edge entropy of each of the one or more motion-compensated reconstructions of the at least part of the scanned region; and adjusting the machine-learning model based on the respective edge entropies.

DESCRIPTION

Figure 1A:
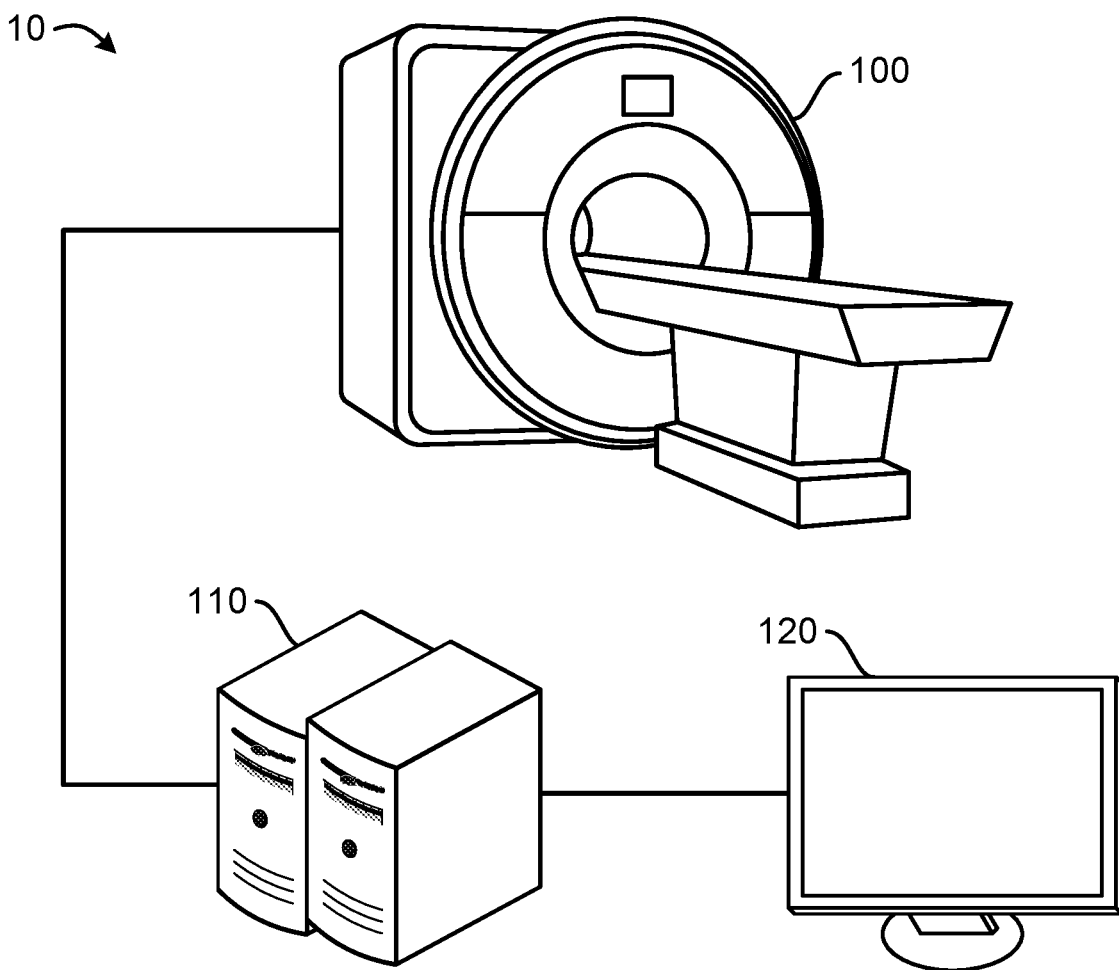
FIG. 1A illustrates an example embodiment of a medical-imaging system.

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein. Furthermore, some embodiments include features from two or more of the following explanatory embodiments.

Also, as used herein, the conjunction "or" generally refers to an inclusive "or," although "or" may refer to an exclusive "or" if expressly indicated or if the context indicates that the "or" must be an exclusive "or."

Additionally, in this description and the drawings, an alphabetic suffix on a reference number may be used to indicate one or more specific instances of the feature identified by the reference numeral. For example, partial reconstructions may be identified with the reference numeral 1021 when a particular partial reconstruction is not being distinguished. However, 1021A may be used to identify one or more specific partial reconstructions or when the one or more specific partial reconstructions are being distinguished from other partial reconstructions.

FIG. 1A illustrates an example embodiment of a medical-imaging system 10. The medical-imaging system 10 includes at least one scanning device 100; one or more image-generation devices 110, each of which is a specially-configured computing device (e.g., a specially-configured desktop computer, a specially-configured laptop computer, a specially-configured server); and a display device 120.

The scanning device 100 is configured to acquire scan data by scanning a region (e.g., area, volume, slice) of an object (e.g., a patient). The scanning modality may be, for example, computed tomography (CT), positron emission tomography (PET), X-ray radiography, magnetic resonance imaging (MRI), and ultrasonography.

The one or more image-generation devices 110 obtain scan data from the scanning device 100 and generate a reconstruction of the scanned region based on the scan data. Also, the reconstruction includes one or more reconstructed images of the scanned region. To generate the reconstruction, for example when the scan data includes groups of scan data that were acquired at different angles or positions, the one or more image-generation devices 110 perform a reconstruction process on the scan data. Examples of reconstruction processes include filtered back projection (e.g., Radon transform) and iterative reconstruction.

After the one or more image-generation devices 110 generate the reconstruction of the scanned region, the one or more image-generation devices 110 send the reconstruction to the display device 120, which displays one or more reconstructed images from the reconstruction.

When scanning a scanned region (e.g., a scanned region of an object), some of the components of the scanning device 100 may move. For example, a radiation emitter and a radiation detector that are positioned on opposite sides of an object may move while scanning the object. The generated scan data includes groups of scan data, each of which was acquired at a respective angle. However, the object may move while the radiation emitter and the radiation detector are moving and scanning the object, which may cause the groups of scan data to acquire scan data of the object while the object is in different positions. For example, if the scanning device 100 is a CT scanner and if the object is a beating heart or a cardiac vessel (e.g., a coronary artery), the heart or cardiac vessel may move while the CT scanner acquires scan data from multiple angles. Accordingly, a reconstructed image of the object may be blurred.

The one or more image-generation devices 110 are configured to use one or more machine-learning models to compensate for any motion in a scanned region, and thereby remove at least some of the blur from the reconstructed images. The one more machine-learning models may include one or more neural networks, such as deep neural networks and convolutional neural networks.

Also, some embodiments of the one or more image-generation devices 110 allow motion correction to be enabled and disabled. For example, some embodiments of the scanning device 100 use cardiac signal monitoring (e.g., electrocardiography) when scanning, which may reduce motion blur in the scanned region. Also for example, some embodiments of the scanning device 100 use cardiac signal monitoring when scanning a heart in order to capture groups of scanned data when the heart is at or close to its quiet phase. However, this may cause the scanning process to consume more time (operate more slowly). Also, if the heart rate changes during scanning, timing the acquisition of the scanned data so that the heart is in the same position each time that scan data is acquired could be difficult. Consequently, scanned data that is acquired using cardiac signal monitoring may still include motion blur (even if the motion blur is reduced). Thus, because motion correction may or may not be desired in various circumstances, some embodiments of the one or more image-generation devices 110 allow motion correction to be enabled and disabled.

Figure 1B:
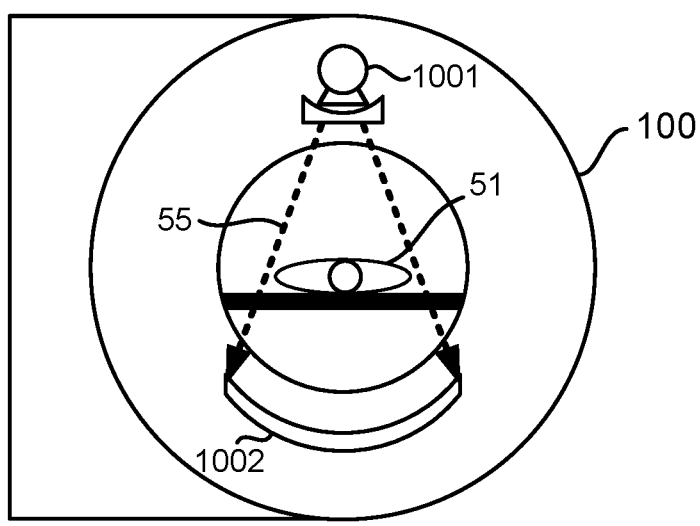
FIG. 1B illustrates an example embodiment of a scanning device.

FIG. 1B illustrates an example embodiment of a scanning device 100. The scanning device 100 includes a radiation emitter 1001 and a radiation detector 1002, which are positioned on opposite sides of an object 51. The radiation emitter 1001 emits radiation 55 (e.g., x-rays) that travels through a scanned region of the object 51 and is detected by the radiation detector 1002. The radiation detector 1002 generates scan data (e.g., groups of scan data 1011) based on the detected radiation 55. In this embodiment, the radiation emitter 1001 emits the radiation in the form of a tapering beam (e.g., a rectangular pyramid, a square pyramid, a circular cone, an elliptical cone). Additionally, the radiation detector 1002 has a curved detection surface. But, in some embodiments, the radiation emitter 1001 emits the radiation in the form of parallel beams, or the radiation detector 1002 has a flat detection surface.

Also, the radiation emitter 1001 and the radiation detector 1002 are configured to rotate around the object 51. Thus, at different angles relative to the object 51, the radiation emitter 1001 emits radiation 55 that travels through the scanned region of the object 51 and is detected by the radiation detector 1002. And, at each of the angles, the radiation detector 1002 generates a respective group of scan data 1011. The angles collectively define an angular scanning range. For example, in some embodiments, the angular scanning range is 0 to 180°, and in some embodiments the angular scanning range is 0 to 360°. Additionally, some embodiments of the scanning device 100 generate respective groups of scan data at 900 to 1200 angles. Thus, for example, if the scanning device generates groups of scan data at 900 angles that range from 0 to 180° and that are evenly spaced, then the increment between angles would be 0.2°. Also for example, if the scanning device generates groups of scan data at 1200 angles that range from 0 to 360° and that are evenly spaced, then the increment between angles would be 0.3°.

Figure 2:
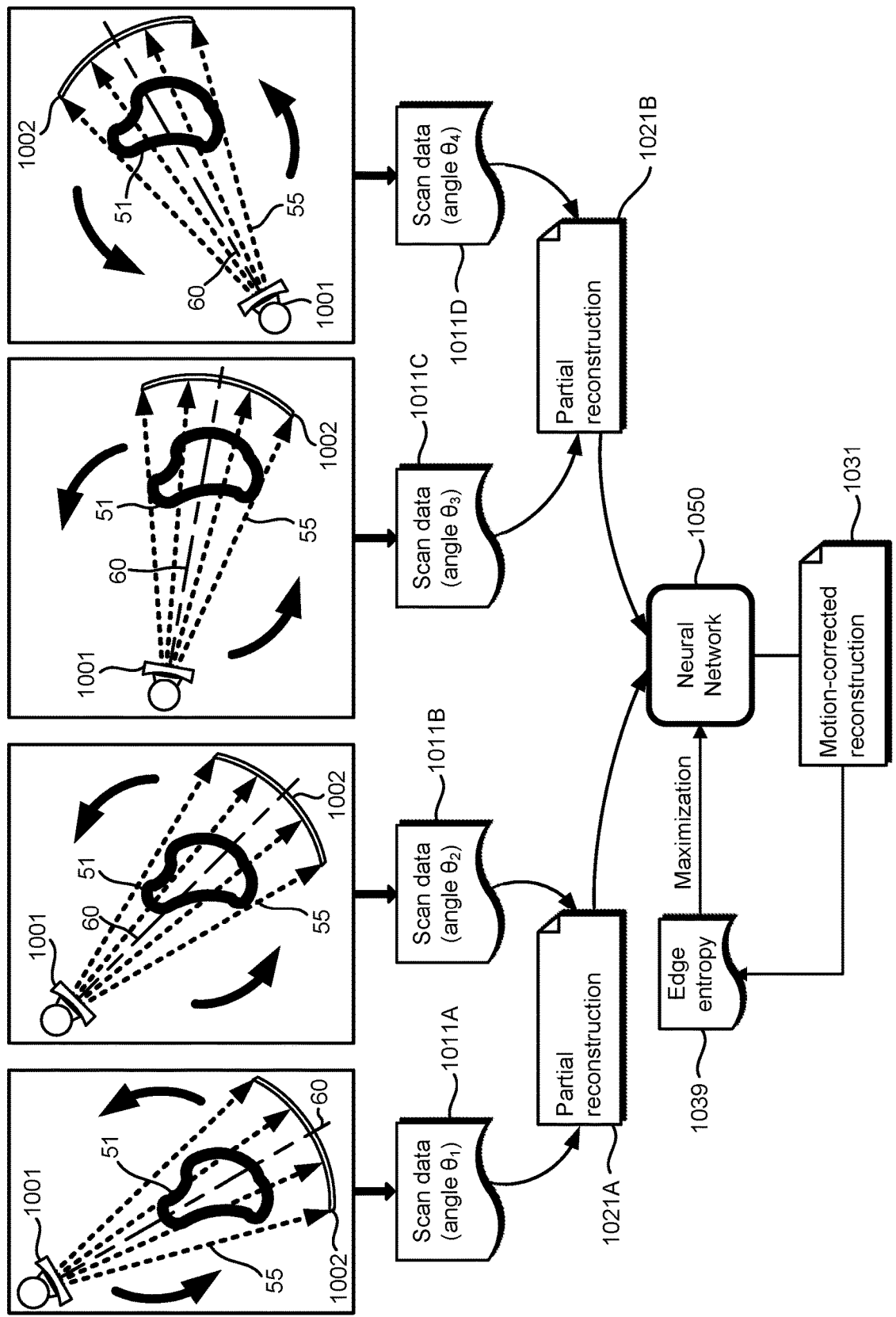
FIG. 2 illustrates an example embodiment of the flow of information in a medical-imaging system.

FIG. 2 illustrates an example embodiment of the flow of information in a medical-imaging system. The system includes a radiation emitter 1001 and a radiation detector 1002, which are positioned on opposite sides of an object 51.

The radiation emitter 1001 emits radiation 55 (e.g., x-rays) that travels through a scanned region of the object 51 and is detected by the radiation detector 1002. The radiation detector 1002 generates groups of scan data 1011 based on the detected radiation 55.

For example, in FIG. 2, the scan data in a first group of scan data 1011A were generated based on radiation that was emitted and detected while an axis 60 between the radiation emitter 1001 and the radiation detector 1002 was at angle $\theta_1$. Also for example, the scan data in a second group of scan data 1011B were generated based on radiation that was emitted and detected while an axis 60 between the radiation emitter 1001 and the radiation detector 1002 was at angle $\theta_2$.

Next, partial reconstructions 1021 of the scanned region are generated based on the groups of scan data 1011. As noted above, examples of reconstruction processes include filtered back projection and iterative reconstruction. In the embodiment in FIG. 2, a first partial reconstruction 1021A is generated based on the first group of scan data 1011A and the second group of scan data 1011B, and a second partial reconstruction 1021B is generated based on a third group of scan data 1011C and a fourth group of scan data 1011D.

If the object was moving as the radiation emitter 1001 and the radiation detector 1002 were emitting radiation and generating scan data (e.g., the object changed its position as the radiation emitter 1001 and the radiation detector 1002 moved to new positions), then the partial reconstructions 1021 will include blurring.

The partial reconstructions 1021 are then input to a machine-learning model, which is a neural network 1050 in this example. The neural network 1050 outputs a motion-corrected reconstruction 1031, which includes one or more motion-corrected reconstructed images of the scanned region of the object 51. Next, the edge entropy 1039 of the motion-corrected reconstruction 1031 is calculated. The edge entropy 1039 is used to train the neural network 1050—the neural network 1050 is trained to maximize the edge entropy 1039. Also, the edge entropy 1039 may be the loss function of the neural network 1050.

Consequently, the machine-learning model (the neural network 1050) can be trained without using ground-truth information (e.g., a ground-truth image). In contrast, some techniques train a machine-learning model by comparing the motion-corrected reconstruction 1031 with a ground-truth image. However, ground-truth images are not available in a clinical setting. Thus, such techniques use simulated ground-truth images to train the machine-learning model. Unlike these techniques, embodiments described herein use edge entropy as the loss function, and thus do not need to use a ground-truth image to train the machine-learning model. Also, the use of edge entropy to train the machine-learning model allows the machine-learning model to be trained using real clinical data instead of simulated data, which may improve the machine-learning model's correction of real motion (as opposed to simulated motion).

Figure 3:
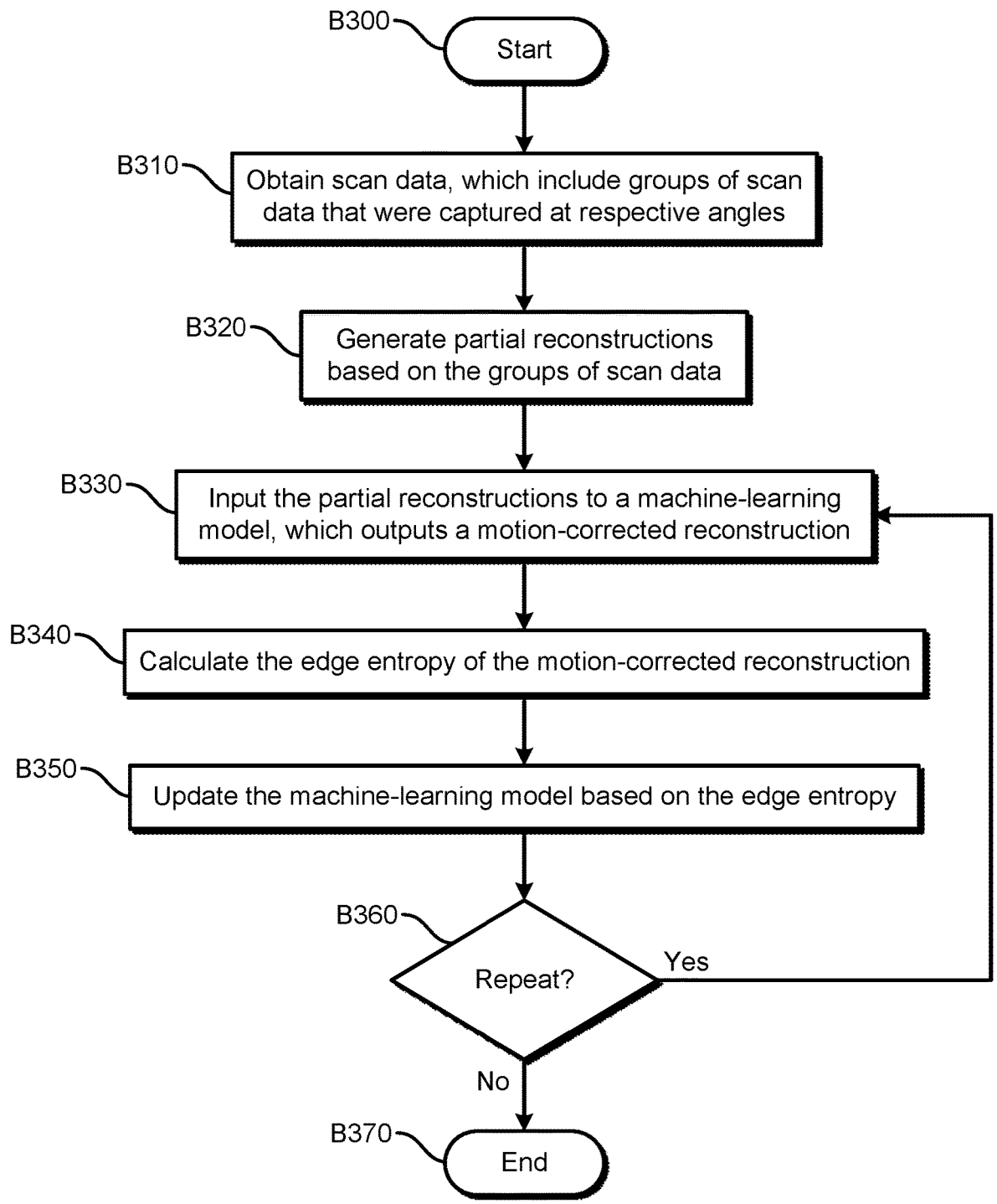
FIG. 3 illustrates an example embodiment of an operational flow for training a machine-learning model.

FIG. 3 illustrates an example embodiment of an operational flow for training a machine-learning model. Although this operational flow and the other operational flows that are described herein are each presented in a certain order, some embodiments may perform at least some of the operations in different orders than the presented orders. Examples of different orders include concurrent, parallel, overlapping, reordered, simultaneous, incremental, and interleaved orders. Thus, other embodiments of the operational flows that are described herein may omit blocks, add blocks, change the order of the blocks, combine blocks, or divide blocks into more blocks.

Furthermore, although this operational flow and the other operational flows that are described herein are performed by an image-generation device, some embodiments of these operational flows are performed by two or more image-generation devices or by one or more other specially-configured computing devices.

The flow begins in block B300 and moves to block B310, where an image-generation device obtains scan data, which include groups of scan data that were captured at respective angles. Next, in block B320, the image-generation device generates partial reconstructions of a scanned region based on the groups of scan data. Each of the partial reconstructions is generated based on one or more respective groups of the groups of scan data. Also, in some embodiments, each group of scan data is used during the generation of one, and only one, partial reconstruction.

The flow then proceeds to block B330, where the image-generation device inputs the partial reconstructions to a machine-learning model, which outputs a motion-corrected reconstruction of the scanned region. In block B340, the image-generation device calculates the edge entropy of the motion-corrected reconstruction. Next, in block B350, the image-generation device updates the machine-learning model based on the edge entropy.

The flow then moves to block B360, where the image-generation device determines whether to repeat blocks B330-B350. If the image-generation device determines to repeat blocks B330-B350 (B360=Yes), then the flow returns to block B330, where the image-generation device inputs the partial reconstructions to the machine-learning model, which was updated in block B350. If the image-generation device determines not to repeat blocks B330-B350 (B360=No), then the flow ends in block B370.

In embodiments where the image-generation device generates a motion-corrected reconstruction of the scanned region without updating the machine-learning model, the flow omits blocks B340-B360.

Figure 4:
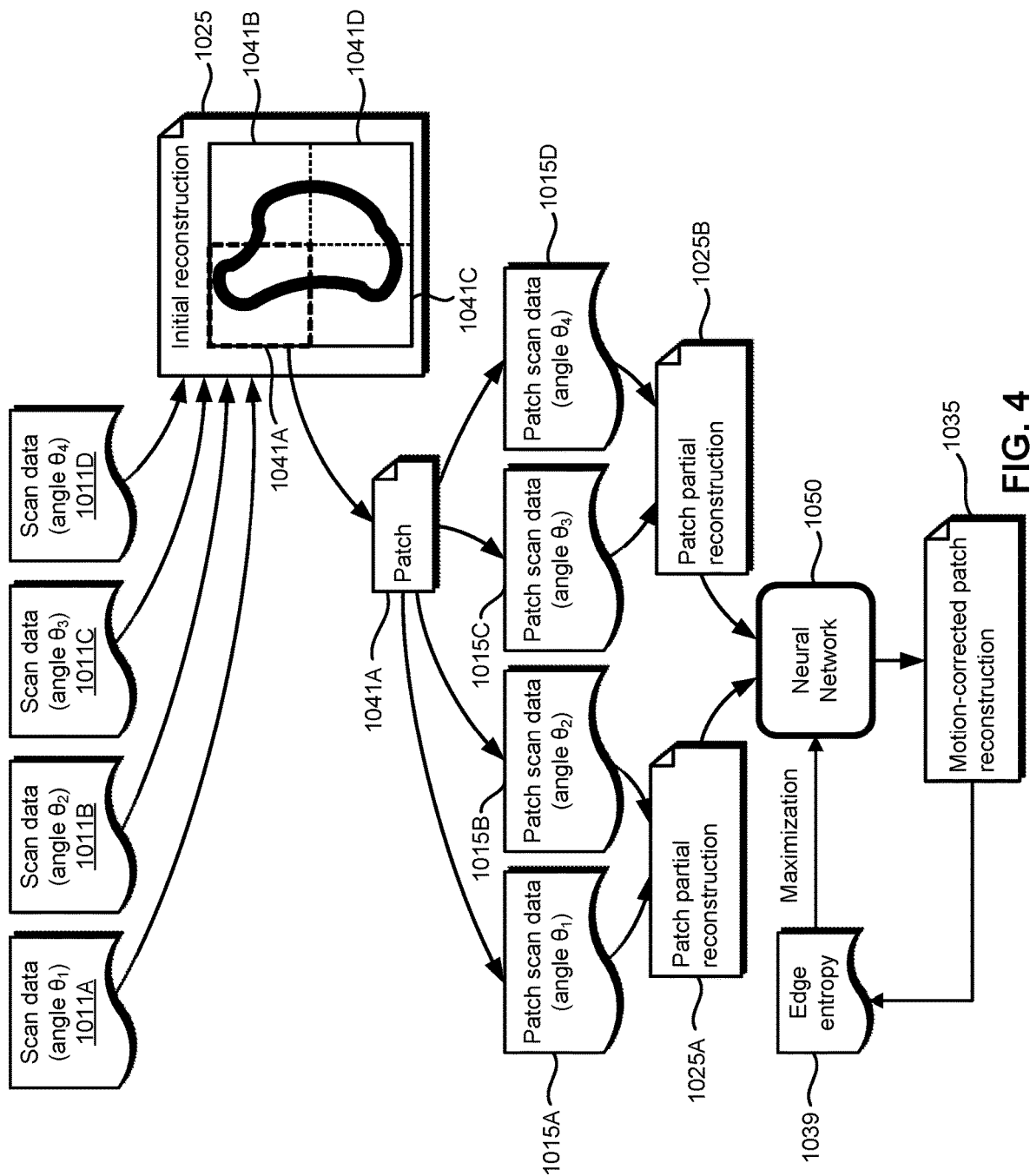
FIG. 4 illustrates an example embodiment of the flow of information in a medical-imaging system.

FIG. 4 illustrates an example embodiment of the flow of information in a medical-imaging system. Scan data 1011 are used to generate an initial reconstruction 1025 of the scanned region. In some embodiments, the initial reconstruction 1025 is a full reconstruction (a complete reconstruction process is performed using all of the scan data 1011) of the scanned region. However, because the initial reconstruction 1025 may be adequate if it can be used to define patches 1041 in the scanned region, in some embodiments the initial reconstruction 1025 is not a full reconstruction. For example, the initial reconstruction 1025 may have been generated by an incomplete reconstruction process that was performed using all of the scan data in the groups of scan data 1011; by a complete reconstruction process that was performed using some, but not all, of the scan data in the groups of scan data 1011; or, alternatively, by an incomplete reconstruction process that was performed using some, but not all, of the scan data in the groups of scan data 1011. Also for example, in some embodiments, the initial reconstruction 1025 is generated using groups of scan data 1011 from a scanning range that is equal to 180° plus the fan angle of the radiation detector. Accordingly, if the fan angle of the radiator detector is 50°, then the initial reconstruction 1025 would be generated using groups of scan data 1011 from a 230° scanning range.

Patches 1041 in the scanned region are then defined using the initial reconstruction 1025 (e.g., the initial reconstruction 1025 may be used to divide the scanned region into patches 1041). Each of the patches 1041 includes a respective portion of the scanned region. In some embodiments, the patches 1041 overlap, and, in some embodiments, the patches 1041 do not overlap. Also, the patches 1041, as well as their sizes and shapes, may be defined according to objects of interest. For example, if the object of interest is a cardiac vessel (e.g., a coronary artery), then patches 1041 that include the cardiac vessel may be defined.

Respective patch partial reconstructions 1025 are then generated for the patches 1041. For example, in FIG. 4, groups of patch scan data 1015 that correspond to a first patch 1041A are used to generate patch partial reconstructions 1025A—B for the first patch 1041A.

A group of patch scan data 1015 includes the scan data from a group of scan data 1011 that correspond to a respective patch 1041 (e.g., the scan data from the portion of the scanned region that corresponds to the patch 1041). For example, in FIG. 3, a first group of patch scan data 1015A includes the scan data from a first group of scan data 1011A that correspond to the first patch 1041A. Thus, the scan data from the first group of scan data 1011A may be used to generate multiple patch partial reconstructions 1025—a respective patch partial reconstruction 1025 for each patch 1041.

Also, multiple patch partial reconstructions 1025 are generated for each patch 1041. Thus, for example, if four patches 1041 are generated, and two patch partial reconstructions 1025 are generated for each patch 1041, then eight patch partial reconstructions 1025 are generated.

The patch partial reconstructions 1025 are then input to a machine-learning model, which is a neural network 1050 in this embodiment. For each patch, the neural network 1050 outputs a respective motion-corrected patch reconstruction 1035 that is based on the respective partial reconstructions 1025 of the patch 1041. Next, the respective edge entropies 1039 of one or more of the patch motion-corrected reconstructions 1035 are calculated. The edge entropies 1039 are used to train the neural network 1050.

Figure 5:
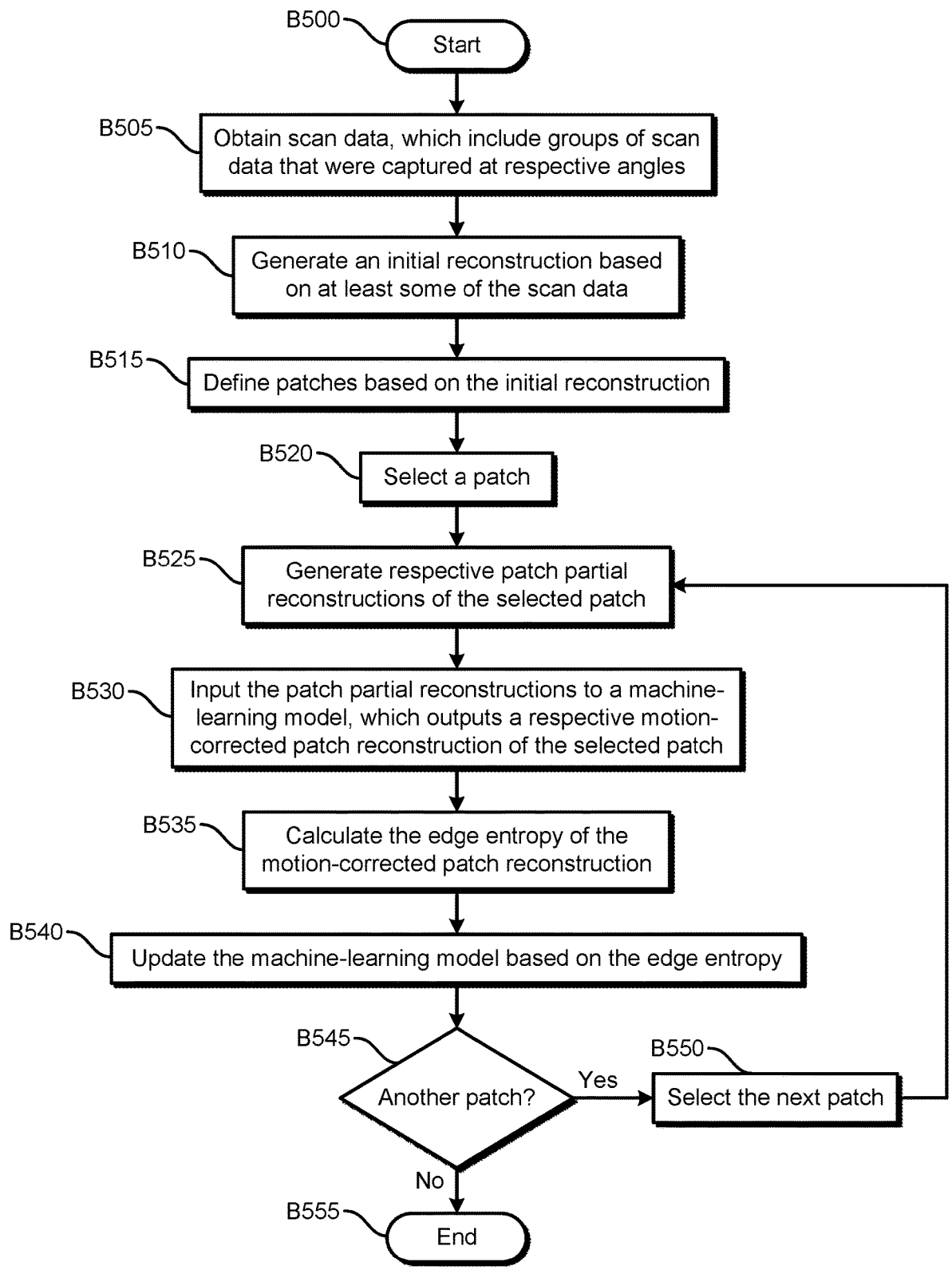
FIG. 5 illustrates an example embodiment of an operational flow for training a machine-learning model.

FIG. 5 illustrates an example embodiment of an operational flow for training a machine-learning model. The flow begins in block B500 and moves to block B505, where an image-generation device obtains scan data, which include groups of scan data that were captured at respective angles. Next, in block B510, the image-generation device generates an initial reconstruction of the scanned region based on at least some of the groups of scan data. The flow then proceeds to block B515, where the image-generation device defines patches in the scanned region based on the initial reconstruction. For example, the image-generation device may divide the initial reconstruction into two or more patches. The sizes and shapes of the patches can be configured for particular applications or circumstances. Thus, for example, the patches may be equally sized, have the same shape, have different sizes, or have different shapes.

Next, in block B520, the image-generation device selects a patch. Then, in block B525, the image-generation device generates respective patch partial reconstructions of the selected patch. Each patch partial reconstruction is generated based on the scan data that correspond to the patch from one or more respective groups of scan data. Also, in some embodiments (e.g., embodiments in which the patches do not overlap), the scan data in each of the respective groups of scan data that correspond to a patch are used during the generation of one, and only one, patch partial reconstruction.

The flow then proceeds to block B530, where the image-generation device inputs the patch partial reconstructions to a machine-learning model, which outputs a respective motion-corrected patch reconstruction of the selected patch. In block B535, the image-generation device calculates the edge entropy of the motion-corrected patch reconstruction. Next, in block B540, the image-generation device updates the machine-learning model based on the edge entropy.

The flow then moves to block B545, where the image-generation device determines whether to repeat blocks B525-B540 for another patch. If the image-generation device determines to repeat blocks B525-B540 for another patch (B545=Yes), then the flow proceeds to block B550. In block B550, the image-generation device selects the next patch, and then the flow returns to block B525. If the image-generation device determines not to repeat blocks B525-B540 for another patch (B545=No) (e.g., if blocks B525-B540 have been performed for every patch), then the flow ends in block B555.

In embodiments where the image-generation device generates a motion-corrected reconstruction without updating the machine-learning model, the flow omits blocks B535-B540, and, in block B555, the image-generation device generates a motion-corrected reconstruction based on the motion-corrected patch reconstructions before the flow ends.

Figure 6:
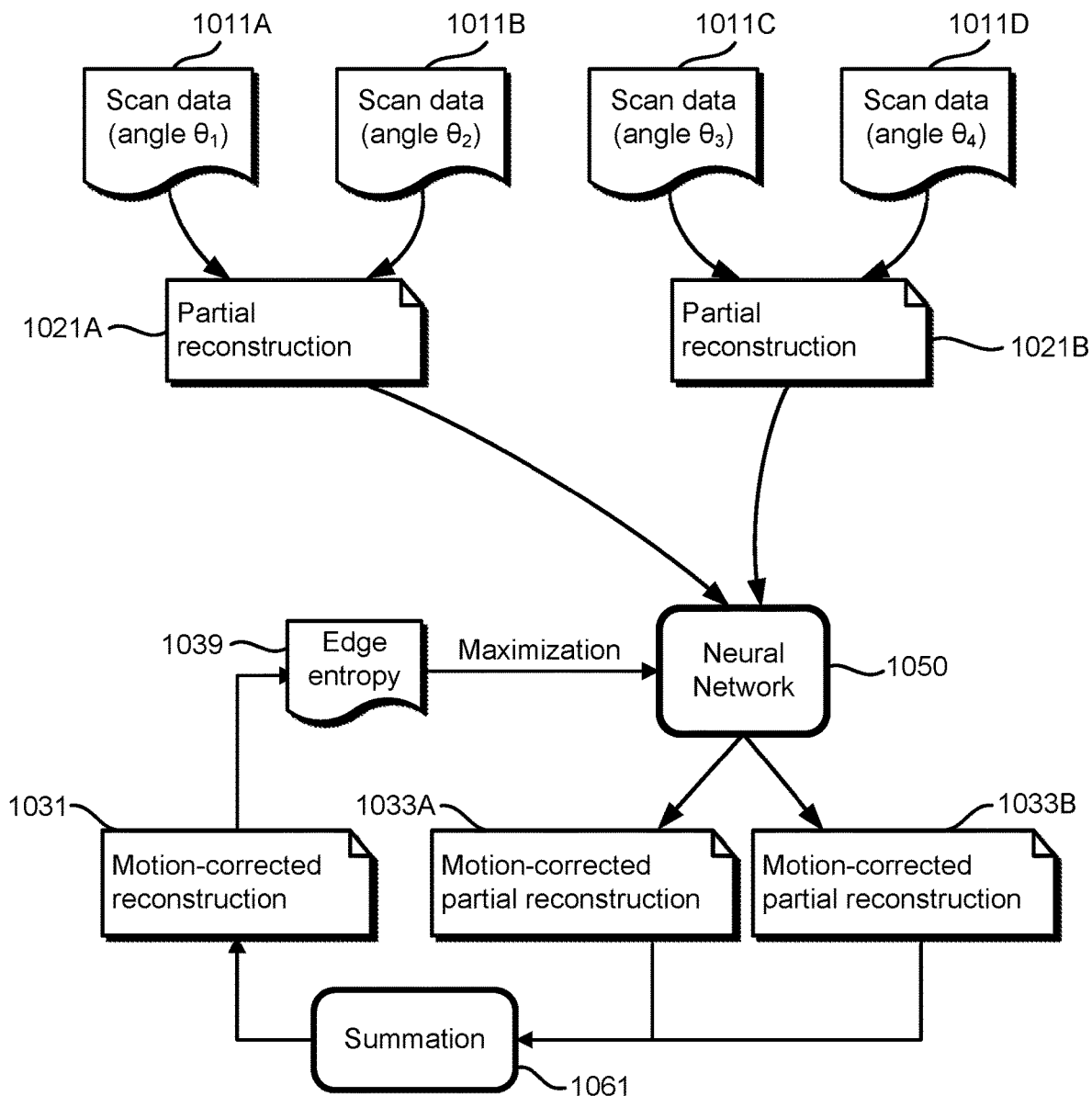
FIG. 6 illustrates an example embodiment of the flow of information in a medical-imaging system.

FIG. 6 illustrates an example embodiment of the flow of information in a medical-imaging system. Groups of scan data 1011 are used to generate partial reconstructions 1021 of a scanned region. In the embodiment in FIG. 6, a first partial reconstruction 1021A is generated based on the first group of scan data 1011A and the second group of scan data 1011B, and a second partial reconstruction 1021B is generated based on a third group of scan data 1011C and a fourth group of scan data 1011D.

The partial reconstructions 1021 are then input to a machine-learning model, which is a neural network 1050 in this example. The partial reconstructions 1021 may be input one by one (e.g., serially). The neural network 1050 outputs a respective motion-corrected partial reconstruction 1033 of each input partial reconstruction 1021. Then a summation 1061 is performed on the motion-corrected partial reconstructions 1033, which produces a motion-corrected reconstruction 1031. Next, the edge entropy 1039 of the motion-corrected reconstruction 1031 is calculated. The edge entropy 1039 is then used to train the neural network 1050.

Figure 7:
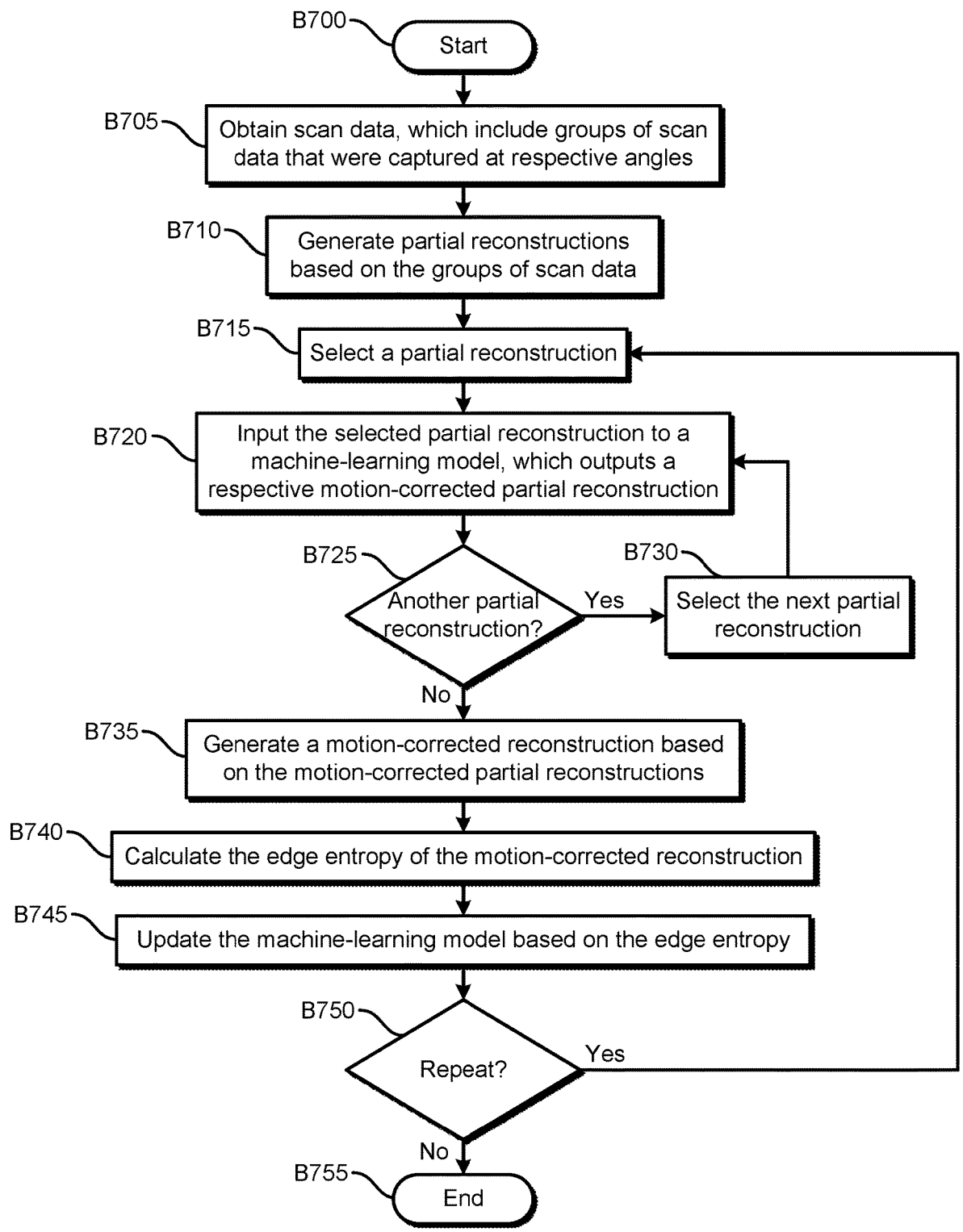
FIG. 7 illustrates an example embodiment of an operational flow for training a machine-learning model.

FIG. 7 illustrates an example embodiment of an operational flow for training a machine-learning model. The flow begins in block B700 and moves to block B705, where an image-generation device obtains scan data, which include groups of scan data that were captured at respective angles. Next, in block B710, the image-generation device generates partial reconstructions of a scanned region based on the groups of scan data. The flow then proceeds to block B715, where the image-generation device selects a partial reconstruction. Then, in block B720, the image-generation device inputs the selected partial reconstruction into a machine-learning model, which outputs a respective motion-corrected partial reconstruction. The flow then proceeds to block B725.

In block B725, the image-generation device determines whether to repeat block B720 for another partial reconstruction (e.g., for a partial reconstruction for which block B720 has not been performed). If the image-generation device determines to repeat block B720 for another partial reconstruction (B725=Yes), then the flow moves to block B730, where the image-generation device selects the next partial reconstruction, and the flow returns to block B720. If the image-generation device determines not to repeat block B720 for another partial reconstruction (B725=No), then the flow advances to block B735.

In block B735, the image-generation device generates a motion-corrected reconstruction of the scanned region based on the motion-corrected partial reconstructions. For example, image-generation device may generated the motion-corrected reconstruction by summing the motion-corrected partial reconstructions such that the value of a pixel in the motion-corrected reconstruction is the sum of the values of the pixels in the motion-corrected partial reconstructions that are located in the same position as the pixel. In block B740, the image-generation device calculates the edge entropy of the motion-corrected reconstruction. Next, in block B745, the image-generation device updates the machine-learning model based on the edge entropy.

The flow then moves to block B750, where the image-generation device determines whether to repeat blocks B715-B745. If the image-generation device determines to repeat blocks B715-B745 (B750=Yes), then the flow returns to block B715. If the image-generation device determines not to repeat blocks B715-B745 (B750=No), then the flow ends in block B755.

In embodiments where the image-generation device generates a motion-corrected reconstruction of the scanned region without updating the machine-learning model, the image-generation device omits blocks B740-B750.

Figure 8:
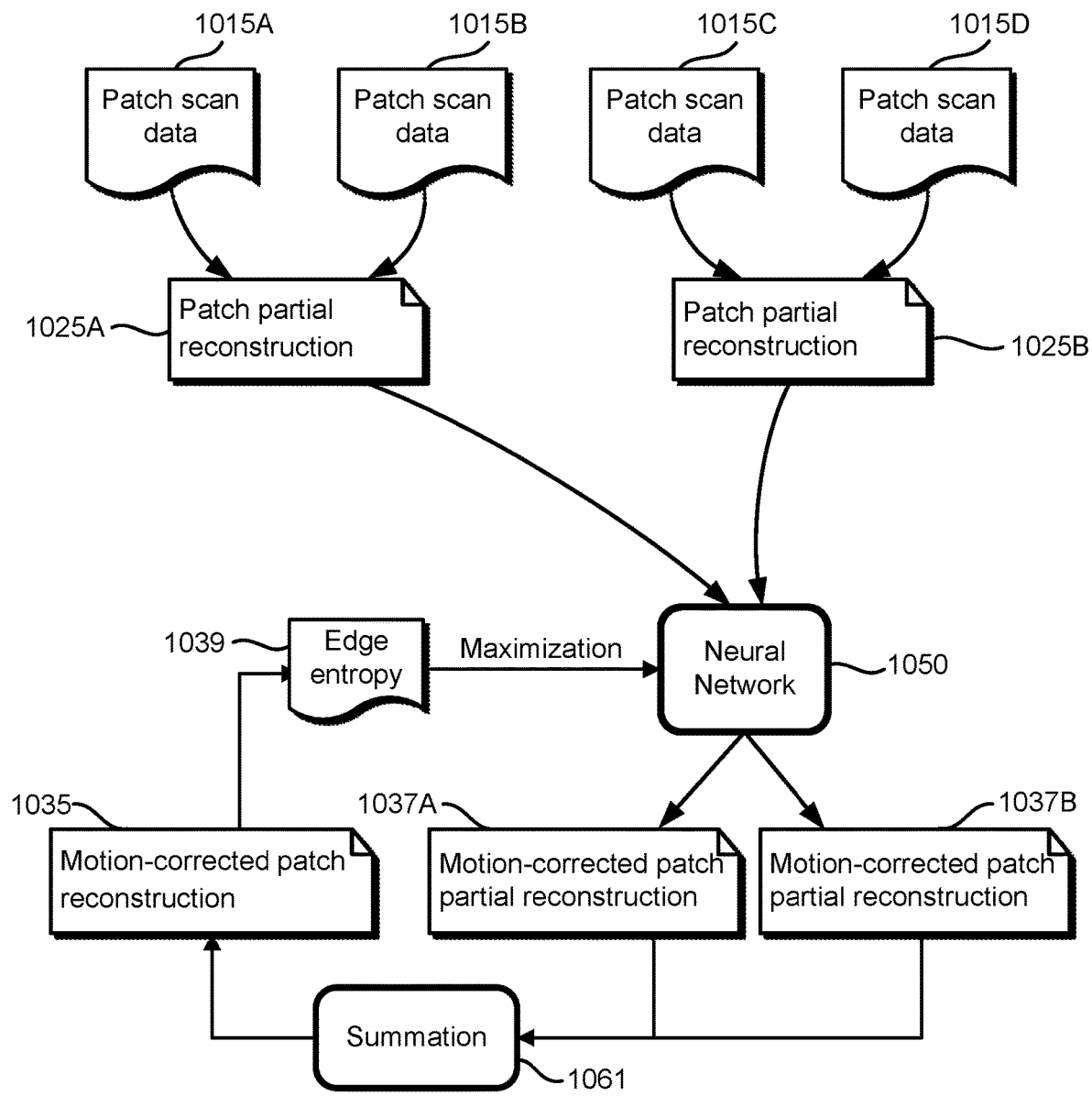
FIG. 8 illustrates an example embodiment of the flow of information in a medical-imaging system.

FIG. 8 illustrates an example embodiment of the flow of information in a medical-imaging system. Groups of patch scan data 1015 are used to generate patch partial reconstructions 1025. For example, in the embodiment in FIG. 8, a first patch partial reconstruction 1025A is generated based on a first group of patch scan data 1015A and on a second group of patch scan data 1015B, and a second patch partial reconstruction 1025B is generated based on a third group of patch scan data 1015C and on a fourth group of patch scan data 1015D.

The patch partial reconstructions 1025 are then input to a machine-learning model, which is a neural network 1050 in this example. The patch partial reconstructions 1025 may be input one by one (e.g., serially). The neural network 1050 outputs a respective motion-corrected patch partial reconstruction 1037 of each input patch partial reconstruction 1025. Then a summation 1061 is performed on the motion-corrected patch partial reconstructions 1037, which produces a motion-corrected patch reconstruction 1035. Next, the edge entropy 1039 of the motion-corrected patch reconstruction 1035 is calculated. The edge entropy 1039 is then used to train the neural network 1050.

Figure 9:
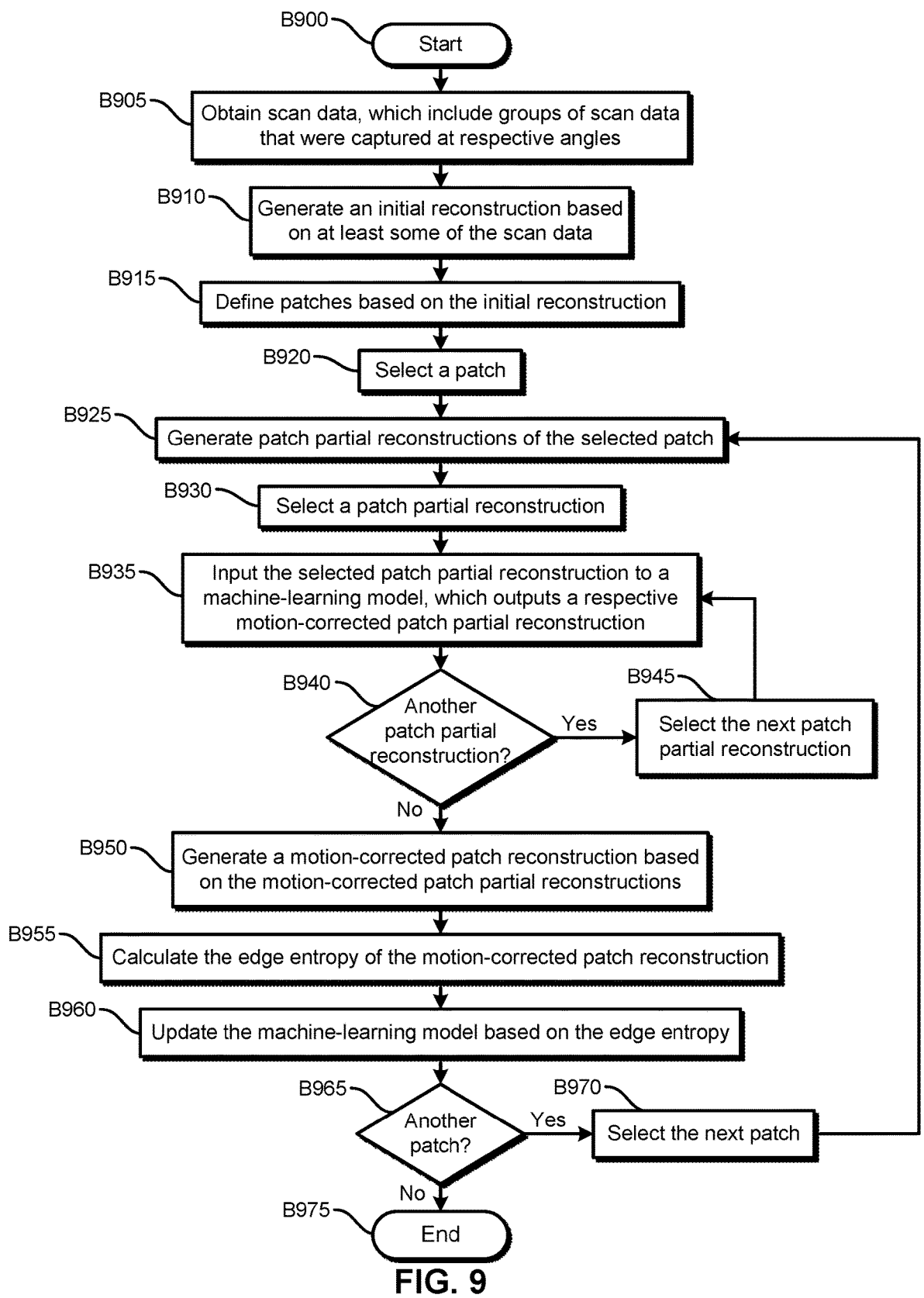
FIG. 9 illustrates an example embodiment of an operational flow for training a machine-learning model.

FIG. 9 illustrates an example embodiment of an operational flow for training a machine-learning model. The flow begins in block B900 and moves to block B905, where an image-generation device obtains scan data, which include groups of scan data that were captured at respective angles. Next, in block B910, the image-generation device generates an initial reconstruction of a scanned region based on at least some of the groups of scan data. The flow then proceeds to block B915, where the image-generation device defines patches in the scanned region based on the initial reconstruction (e.g., divides the initial reconstruction of the scanned region into two or more patches). Next, in block B920, the image-generation device selects a patch.

The flow then advances to block B925, where the image-generation device generates two or more patch partial reconstructions of the selected patch based on the scan data in the groups of scan data that correspond to the selected patch. The flow then proceeds to block B930, where the image-generation device selects a patch partial reconstruction. Then, in block B935, the image-generation device inputs the selected patch partial reconstruction into a machine-learning model, which outputs a respective motion-corrected patch partial reconstruction. The flow then proceeds to block B940.

In block B940, the image-generation device determines if there is a patch partial reconstruction for which block B935 has not been performed. If the image-generation device determines that there is a patch partial reconstruction for which block B935 has not been performed (B940=Yes), then the flow moves to block B945, where the image-generation device selects the next patch partial reconstruction, and the flow returns to block B935. If the image-generation device determines that there is not a patch partial reconstruction for which block B935 has not been performed (B940=No), then the flow advances to block B950.

In block B950, the image-generation device generates a motion-corrected patch reconstruction based on the motion-corrected patch partial reconstructions. For example, the image-generation device may generated the motion-corrected patch reconstruction by summing the motion-corrected patch partial reconstruction such that the value of a pixel in the motion-corrected patch reconstruction is the sum of the values of the pixels in the motion-corrected patch partial reconstructions that are located in the same position as the pixel. In block B955, the image-generation device calculates the edge entropy of the motion-corrected patch reconstruction. Next, in block B960, the image-generation device updates the machine-learning model based on the edge entropy.

The flow then moves to block B965, where the image-generation device determines whether there is at least one patch for which blocks B925-B960 have not been performed. If the image-generation device determines that there is at least one patch for which blocks B925-B960 have not been performed (B965=Yes), then the flow proceeds to block B970, where the image-generation device selects the next patch. The flow then returns to block B925. If the image-generation device determines that there is no patch for which blocks B925-B960 have not been performed (B965=No), then the flow ends in block B975.

In embodiments where the image-generation device generates a motion-corrected reconstruction of the scanned region without updating the machine-learning model, the flow omits blocks B955-B960, and, in block B975, the image-generation device generates a motion-corrected reconstruction of the scanned region based on the motion-corrected patch reconstructions before the flow ends.

Figure 10:
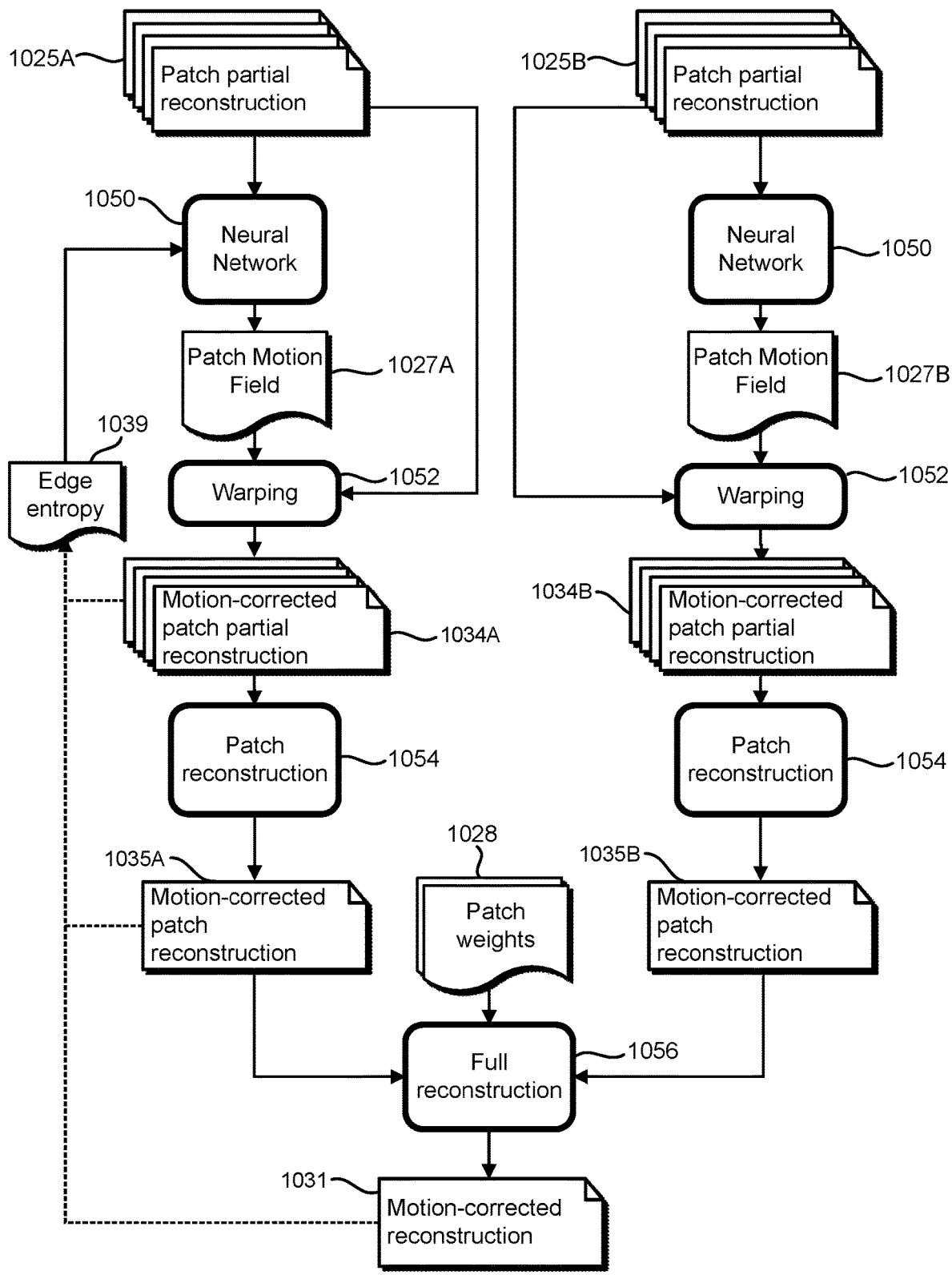
FIG. 10 illustrates an example embodiment of the flow of information in a medical-imaging system.

FIG. 10 illustrates an example embodiment of the flow of information in a medical-imaging system. Patch partial reconstructions 1025 are input to a neural network 1050, which outputs a patch motion field 1027 that is based on the input patch partial reconstructions 1025. For example, a first group of patch partial reconstructions 1025A is input to the neural network 1050, which outputs a patch motion field 1027A that is based on the first group of patch partial reconstructions 1025A. A patch motion field 1027 indicates any respective movements of the pixels or voxels among the patch partial reconstructions 1025. For example, if a first pixel is located at position 1,1 in a first patch partial reconstruction, is located at position 1,2 in a second patch partial reconstruction, and is located at position 2,2 in a third patch partial reconstruction, then the motion field will indicate this movement of the first pixel.

Also, the two neural networks 1050 in FIG. 10 may be identical (e.g., two instances of the same network) or be the same neural network 1050.

Next, a warping operation 1052 is performed on the patch partial reconstructions 1025 based on the patch motion field 1027 that was generated based on the patch partial reconstructions 1025. The warping operation 1052 warps at least some of the patch partial reconstructions 1025 to generate motion-corrected patch partial reconstructions 1034, in which each pixel or voxel has the same or approximately the same location across all of the motion-corrected patch partial reconstructions 1034. For example, in FIG. 10, a warping operation 1052 is performed on a second group of patch partial reconstructions 10256, and the warping operation 1052 is based on the patch motion field 10276 that was generated based on the second group of patch partial reconstructions 10256. The warping operation 1052 generates a second group of motion-corrected patch partial reconstructions 10346.

Next, a patch reconstruction operation 1054 is performed on a patch's motions-corrected patch partial reconstructions 1034, thereby generating a motion-corrected patch reconstruction 1035. For example, in FIG. 10, a patch reconstruction operation 1054 is performed on a first group of motion-corrected patch partial reconstructions 1034A, which generates a first motion-corrected patch reconstruction 1035A. Also, a patch reconstruction operation 1054 is performed on a second group of motion-corrected patch partial reconstructions 1034B, which generates a second motion-corrected patch reconstruction 10356.

A full reconstruction operation 1056, which may include combining and smoothing operations, is then performed on two or more motion-corrected patch reconstructions 1035. The full reconstruction operation 1056 combines the motion-corrected patch reconstructions 1035 into a single motion-corrected reconstruction 1031 and smooth the values in the motion-corrected reconstruction 1031, for example along the boundaries between the motion-corrected patch reconstructions 1035. FIG. 10 shows a full reconstruction operation 1056 that is performed on the first motion-corrected patch reconstruction 1035A and the second motion-corrected patch reconstruction 10356 to generate the motion-corrected reconstruction 1031.

The full reconstruction operation 1056 may be further based on one or more patch weights 1028. In some embodiments, patches that include some of an object of interest (e.g., organ, cardiac vessel) are given larger patch weights 1028 than patches that do not include any part of an object of interest. A patch weight 1028 indicates a weight that a corresponding motion-corrected patch reconstruction 1035 is given in the combining and smoothing operations. When a motion-corrected patch reconstruction has a larger corresponding weight 1028, that may indicate that, when combining and smoothing the motion-corrected patch reconstruction with another motion-corrected patch reconstruction, the motion-corrected patch reconstruction's values should be changed less than the values of the other motion-corrected patch reconstruction. For example, if the first motion-corrected patch reconstruction 1035A has a larger corresponding weight 1028 than the second motion-corrected patch reconstruction 10356, when the first motion-corrected patch reconstruction 1035A and the second motion-corrected patch reconstruction 1035B are combined and smoothed, the values of the first motion-corrected patch reconstruction 1035A may be changed less than (including no change) the values in the second motion-corrected patch reconstruction 1035B.

Additionally, the edge entropy 1039 may be calculated for one or more motion-corrected patch partial reconstructions 1034, may be calculated for one or more motion-corrected patch reconstructions 1035, or may be calculated for the motion-corrected reconstruction 1031. The edge entropy 1039 is used to retrain the neural network 1050.

Figure 11:
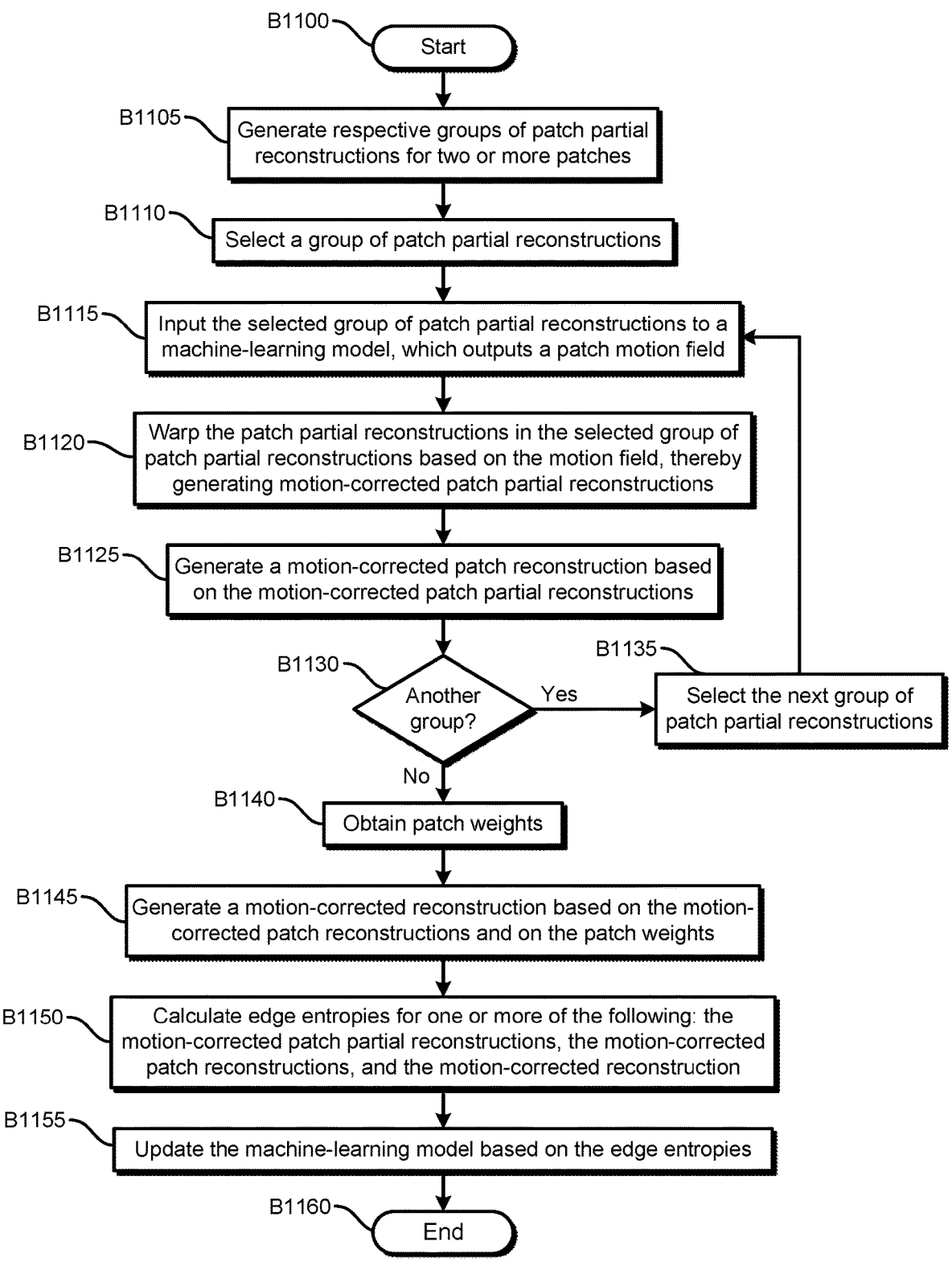
FIG. 11 illustrates an example embodiment of an operational flow for training a machine-learning model.

FIG. 11 illustrates an example embodiment of an operational flow for training a machine-learning model. The flow starts in block B1100 and moves to block B1105, where an image-generation device generates or otherwise obtains respective groups of patch partial reconstructions for two or more patches. The flow then moves to block B1110, where the image-generation device selects a group of patch partial reconstructions.

Next, in block B1115, the image-generation device inputs the selected group of patch partial reconstructions to a machine-learning model, which outputs a patch motion field. The flow advances to block B1120, where the image-generation device warps the patch partial reconstructions in the selected group of patch partial reconstructions based on the motion field, thereby generating motion-corrected patch partial reconstructions. Then, in block B1125, the image-generation device generates a motion-corrected patch reconstruction based on the motion-corrected patch partial reconstructions. For example, the image-generation device may sum the motion-corrected patch partial reconstructions to generate the motion-corrected patch reconstruction.

The flow then advances to block B1130, where the image-generation device determines whether there is another group of patch partial reconstructions on which blocks B1115-B1125 have not been performed. If the image-generation device determines that there is another group of patch partial reconstructions on which blocks B1115-B1125 have not been performed (B1130=Yes), then the flow proceeds to block B1135, where the image-generation device selects the next group of patch partial reconstructions. The flow then returns to block B1115. If the image-generation device determines that there is not another group of patch partial reconstructions on which blocks B1115-B1125 have not been performed (B1130=No), then the flow advances to block B1140.

In block B1140, the image-generation device obtains respective patch weights for the two or more patches. Then, in block B1145, the image-generation device generates a motion-corrected reconstruction of the scanned region based on the motion-corrected patch reconstructions and on the patch weights. For example, the image-generation device may combine the patches and smooth the boundaries of the patches. During the smoothing, the image-generation device may alter a patch more or less, depending on the weight of the patch and the weight of the neighboring patches.

Next, in block B1150, the image-generation device calculate the edge entropy of one or more of the following: the motion-corrected patch partial reconstructions, the motion-corrected patch reconstructions, and the motion-corrected reconstruction. The flow then moves to block B1155, where the image-generation device updates the machine-learning model based on the edge entropies. The flow then ends in block B1160.

In embodiments where the image-generation device generates a motion-corrected reconstruction without updating the machine-learning model, the image-generation device omits blocks B1150 and B1155.

Figure 12:
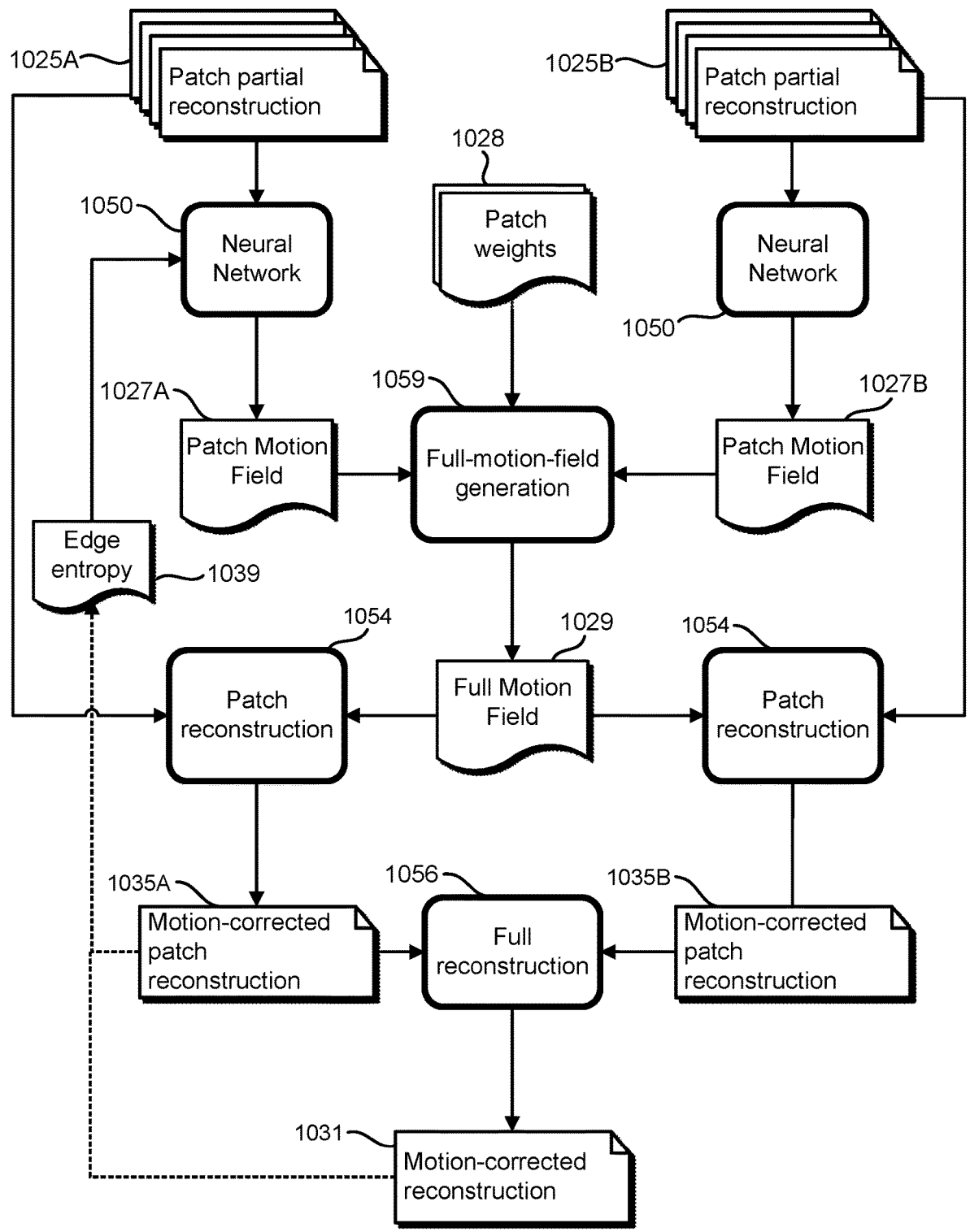
FIG. 12 illustrates an example embodiment of the flow of information in a medical-imaging system.

FIG. 12 illustrates an example embodiment of the flow of information in a medical-imaging system. Patch partial reconstructions 1025 are input to a neural network 1050, which outputs a patch motion field 1027 that is based on the input patch partial reconstructions 1025. For example, a first group of patch partial reconstructions 1025A is input to the neural network 1050, which outputs a patch motion field 1027A that is based on the first group of patch partial reconstructions 1025A.

Also, the two neural networks 1050 in FIG. 10 may be identical (e.g., two instances of the same network) or be the same neural network 1050 (e.g., the groups of patch partial reconstructions may be input one at a time).

Then a full-motion-field generation operation 1059 generates a full motion field 1029 based on the patch motion fields 1027 and, in some embodiments, on patch weights 1028. The full motion field 1029 is a motion field for a complete reconstruction. The full-motion-field generation operation 1059 combines the patch motion fields 1027 and may also performing smoothing or interpolation. When a patch motion field 1027 has a larger corresponding weight 1028, that may indicate that, when combining and smoothing the patch motion field 1027 with another patch motion field 1027, the patch motion field's values should be changed less than the values of the other patch motion field. For example, if the first patch motion field 1027A has a larger corresponding weight 1028 than the second patch motion field 1027B, when the first patch motion field 1027A and the second patch motion field 1027B are combined and smoothed, the values of the first patch motion field 1027A may be changed less than (including no change) the values in the second patch motion field 1027B.

Next, a patch reconstruction operation 1054 is performed for each patch based on the patch's group of patch partial reconstructions 1025 and on the full motion field 1029. The patch reconstruction operation 1054 sums the patch partial reconstructions 1025 and may warp at least some of the patch partial reconstructions 1025 according to the full motion field 1029. The patch reconstruction operation 1054 generates a motion-corrected patch reconstruction 1035. For example, in FIG. 12, a patch reconstruction operation 1054 is performed on a first group of patch partial reconstructions 1025A, and the patch reconstruction operation 1054 is based on the full motion field 1029. The patch reconstruction operation 1054 generates a first motion-corrected patch reconstruction 1035A. Also, a patch reconstruction operation 1054 is performed on a second group of patch partial reconstructions 1025B, which generates a second motion-corrected patch reconstruction 1035B.

A full reconstruction operation 1056 is then performed on two or more motion-corrected patch reconstructions 1035. FIG. 12 shows a full reconstruction operation 1056 that is performed on the first motion-corrected patch reconstruction 1035A and the second motion-corrected patch reconstruction 1035B, and the operation generates a motion-corrected reconstruction 1031 of the scanned region.

Additionally, an edge entropy 1039 may be calculated for one or more motion-corrected patch reconstructions 1035 or may be calculated for the motion-corrected reconstruction 1031. The edge entropy 1039 is used to retrain the neural network 1050.

Figure 13:
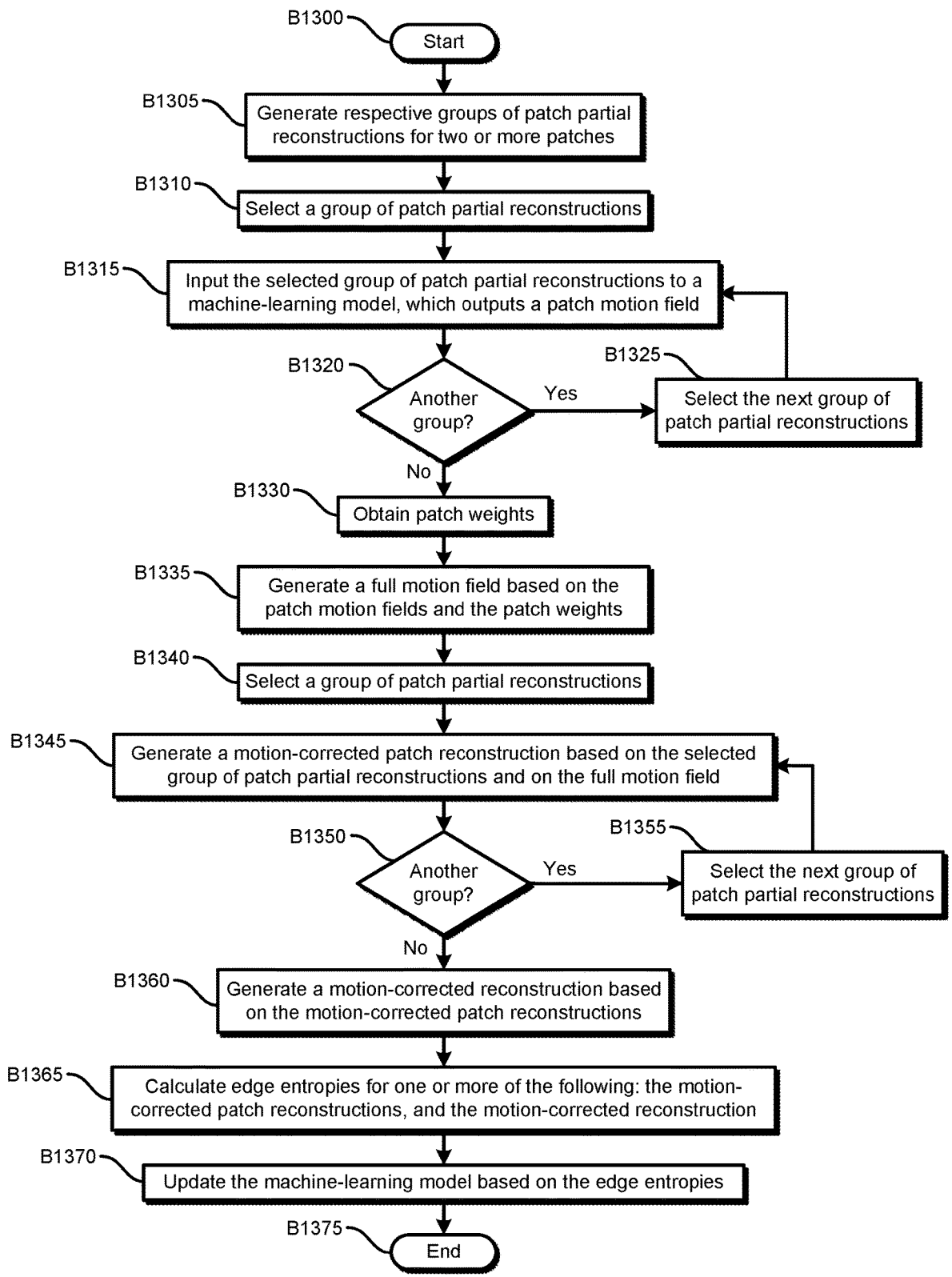
FIG. 13 illustrates an example embodiment of an operational flow for training a machine-learning model.

FIG. 13 illustrates an example embodiment of an operational flow for training a machine-learning model. The flow starts in block B1300 and then proceeds to block B1305, where an image-generation device generates respective groups of patch partial reconstructions for two or more patches. Next, in block B1310, the image-generation device selects a group of patch partial reconstructions. Then, in block B1315, the image-generation device inputs the selected group of patch partial reconstructions to a machine-learning model, which outputs a patch motion field for the patch.

The flow then moves to block B1320, where the image-generation device determines whether there is a group of patch partial reconstructions for which block B1315 has not been performed. If the image-generation device determines that there is a group of patch partial reconstructions for which block B1315 has not been performed (B1320=Yes), then the flow moves to block B1325, where the image-generation device selects the next group of patch partial reconstructions, and the flow then returns to block B1315. If the image-generation device determines that there is not a group of patch partial reconstructions for which block B1315 has not been performed (B1320=No), then the flow proceeds to block B1330.

In block B1330, the image-generation device obtains patch weights. Next, in block B1335, the image-generation device generates a full motion field based on the patch motion fields and on the patch weights.

The flow then advances to block B1340, where the image-generation device selects a group of patch partial reconstructions. Next, in block B1345, the image-generation device generates a motion-corrected patch reconstruction based on the selected group of patch partial reconstructions and on the full motion field. The flow then moves to block B1350, where the image-generation device determines whether there is a group of patch partial reconstructions (or a patch) for which block B1345 has not been performed. If the image-generation device determines that there is a group of patch partial reconstructions (or a patch) for which block B1345 has not been performed (B1350=Yes), then the flow moves to block B1355, where the image-generation device selects the next group of patch partial reconstructions, and the flow then returns to block B1345. If the image-generation device determines that there is not a group of patch partial reconstructions (or a patch) for which block B1345 has not been performed (B1350=No), then the flow proceeds to block B1360.

In block B1360, the image-generation device generates a motion-corrected reconstruction of the scanned region based on the motion-corrected patch reconstructions. Then, in block B1365, the image-generation device calculates a respective edge entropy for one or more of the following: the motion-corrected patch reconstructions, and the motion corrected reconstruction. Next, in block B1370, the image-generation device updates the machine-learning model based on the edge entropies. The flow then ends in block B1375.

In embodiments where the image-generation device generates a motion-corrected reconstruction without updating the machine-learning model, the image-generation device omits blocks B1365 and B1370.

Figure 14:
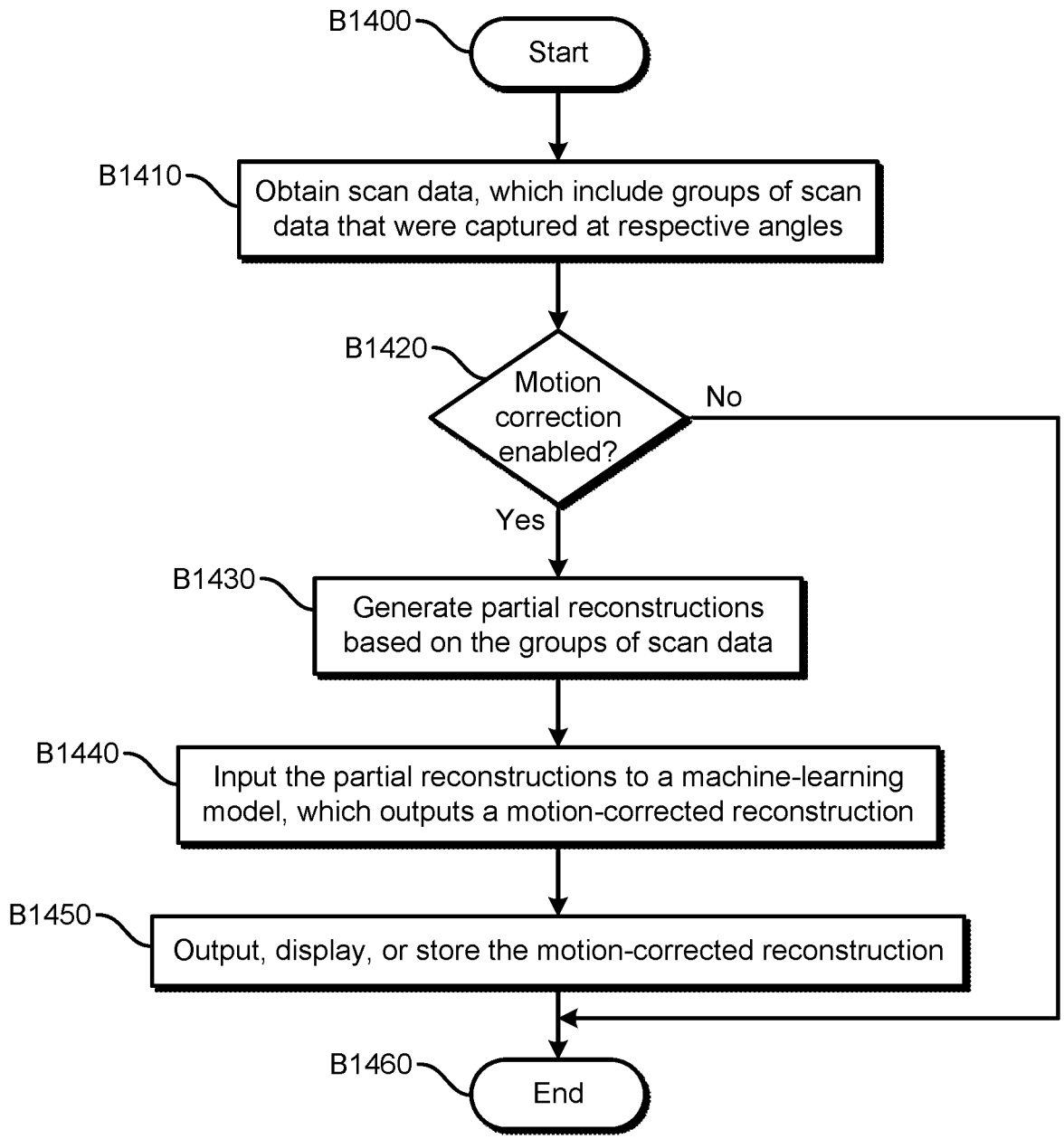
FIG. 14 illustrates an example embodiment of an operational flow for generating a motion-corrected reconstruction.

FIG. 14 illustrates an example embodiment of an operational flow for generating a motion-corrected reconstruction of a scanned region. The flow begins in block B1400 and moves to block B1410, where an image-generation device obtains scan data, which include groups of scan data that were captured at respective angles. Next, in block B1420, the image-generation device determines whether motion correction is enabled (e.g., whether a motion-correction setting is set to enabled). If the image-generation determines that motion correction is enabled (B1420=Yes), then the flow moves to block B1430. If the image-generation determines that motion correction is not enabled (B1420=No), then the flow moves to block B1460.

In block B1430, the image-generation device generates partial reconstructions of a scanned region based on the groups of scan data. The flow then proceeds to block B1440, where the image-generation device inputs the partial reconstructions to a machine-learning model, which outputs a motion-corrected reconstruction of the scanned region. In block B1450, the image-generation device outputs, displays, or stores the motion-corrected reconstruction. Then the flow ends in block B1460.

Figure 15:
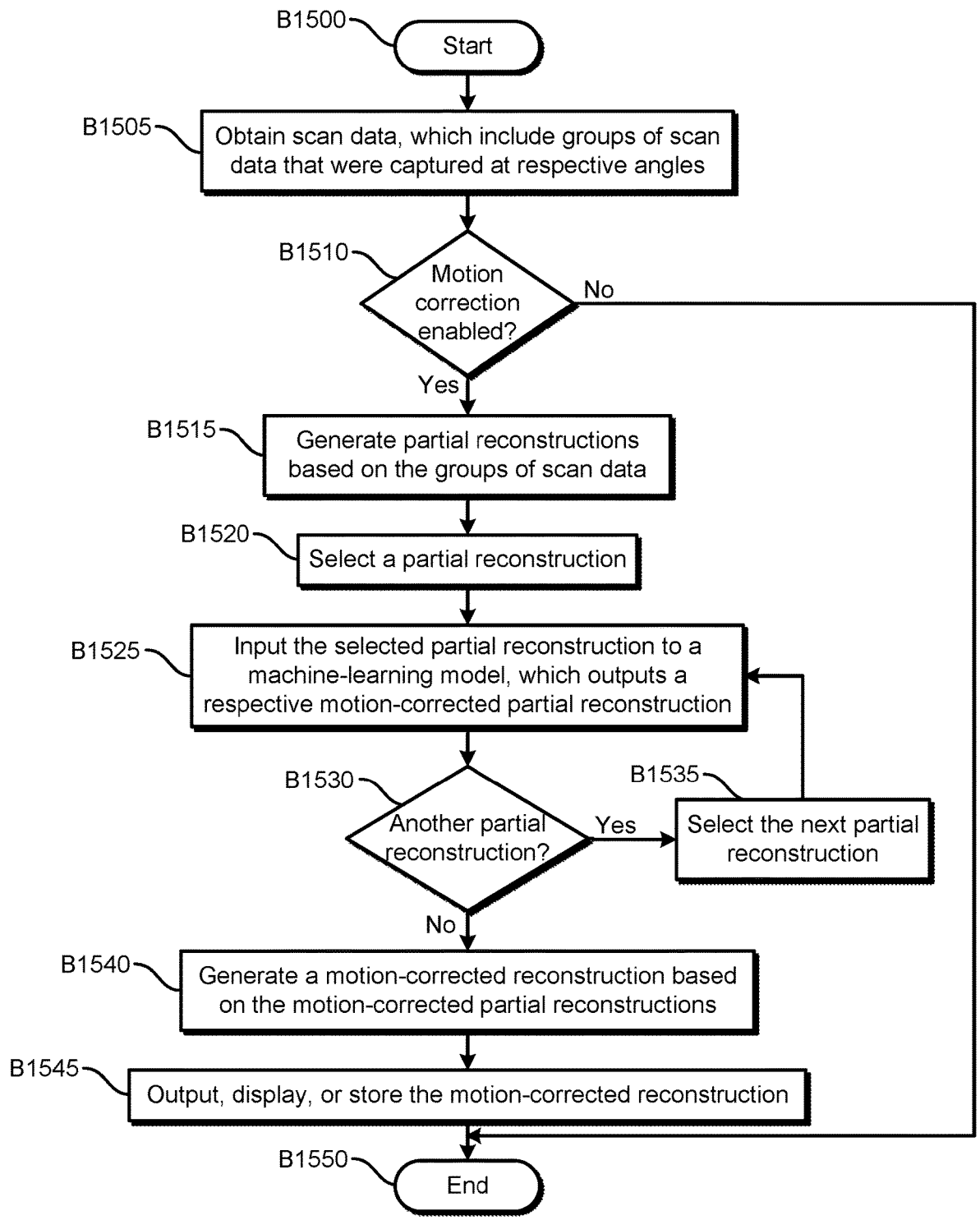
FIG. 15 illustrates an example embodiment of an operational flow for generating a motion-corrected reconstruction.

FIG. 15 illustrates an example embodiment of an operational flow for generating a motion-corrected reconstruction of a scanned region. The flow begins in block B1500 and moves to block B1505, where an image-generation device obtains scan data, which include groups of scan data that were captured at respective angles.

Next, in block B1510, the image-generation device determines whether motion correction is enabled. If the image-generation determines that motion correction is enabled (B1510=Yes), then the flow moves to block B1515. If the image-generation determines that motion correction is not enabled (B1510=No), then the flow moves to block B1550.

Next, in block B1515, the image-generation device generates partial reconstructions of a scanned region based on the groups of scan data. The flow then proceeds to block B1520, where the image-generation device selects a partial reconstruction. Then, in block B1525, the image-generation device inputs the selected partial reconstruction into a machine-learning model, which outputs a respective motion-corrected partial reconstruction. The flow then proceeds to block B1530.

In block B1530, the image-generation device determines whether to repeat block B1525 for another partial reconstruction (e.g., for a partial reconstruction for which block B1525 has not been performed). If the image-generation device determines to repeat block B1525 for another partial reconstruction (B1530=Yes), then the flow moves to block B1535, where the image-generation device selects the next partial reconstruction, and the flow returns to block B1525. If the image-generation device determines not to repeat block B1525 for another partial reconstruction (B1530=No), then the flow advances to block B1540.

In block B1540, the image-generation device generates a motion-corrected reconstruction of the scanned region based on the motion-corrected partial reconstructions. Also, in block B1545 the image-generation device outputs, displays, or stores the motion-corrected reconstruction of the scanned region. The flow then ends in block B1550.

Figure 16:
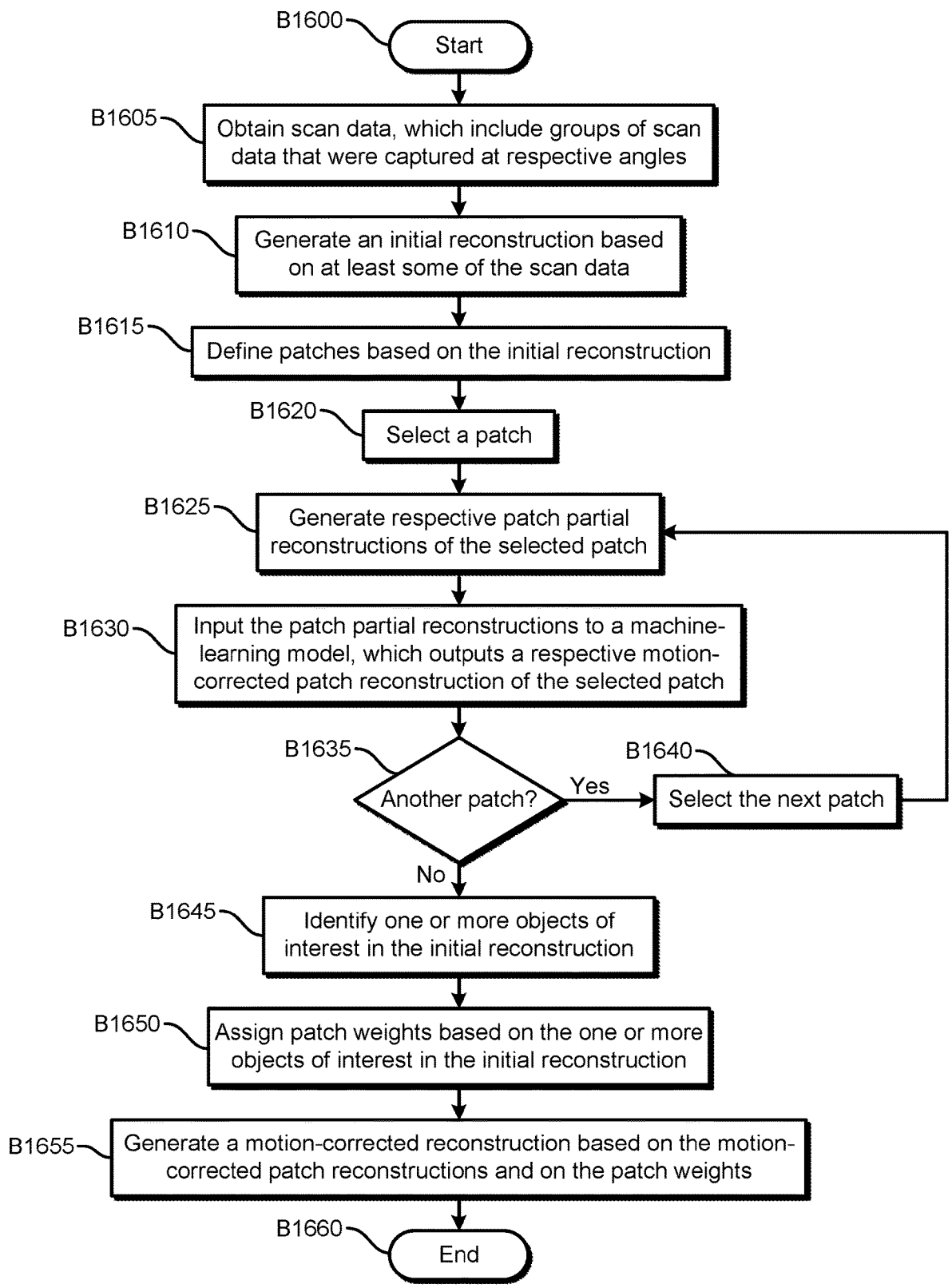
FIG. 16 illustrates an example embodiment of an operational flow for generating a motion-corrected reconstruction.

FIG. 16 illustrates an example embodiment of an operational flow for generating a motion-corrected reconstruction of a scanned region. The flow begins in block B1600 and moves to block B1605, where an image-generation device obtains scan data, which include groups of scan data that were captured at respective angles. Next, in block B1610, the image-generation device generates an initial reconstruction of the scanned region based on at least some of the groups of scan data. The flow then proceeds to block B1615, where the image-generation device defines patches in the scanned region based on the initial reconstruction.

Next, in block B1620, the image-generation device selects a patch. Then, in block B1625, the image-generation device generates respective patch partial reconstructions of the selected patch. The flow then proceeds to block B1630, where the image-generation device inputs the patch partial reconstructions to a machine-learning model, which outputs a respective motion-corrected patch reconstruction of the selected patch. The flow then moves to block B1635, where the image-generation device determines whether to repeat blocks B1625-B1630 for another patch. If the image-generation device determines to repeat blocks B1625-B1630 for another patch (B1635=Yes), then the flow proceeds to block B1640. In block B1640, the image-generation device selects the next patch, and then the flow returns to block B1625. If the image-generation device determines not to repeat blocks B1625-B1630 for another patch (B1635=No) (e.g., if blocks B1625-B1630 have been performed for every patch), then the flow proceeds to block B1645.

In block B1645, the image-generation device identifies one or more objects of interest in the initial reconstruction. For example, the object of interest may a coronary vessel, a ventricle, or a coronary valve. The image-generation device also identifies patches that include at least part of an object of interest and patches that do not include any part of an object of interest.

Next, in block B1650, the image-generation device assign patch weights to the patches based on the one or more objects of interest. For example, the image-generation device may assign higher patch weights to the patches that include at least some of an object of interest than to the patches that do not include any part of an object of interest. Also, the patch weight of a patch may be proportional to the amount of the one or more objects of interest that the patch includes. And the objects of interest may have different respective object weights (e.g., higher weights for object of greater interest), and the patch weights may be based on the object weights (e.g., a patch that includes an object that has a greater object weight may have a greater patch weight than a patch that includes an object that has a lower object weight).

The flow then advances to block B1655, where the image-generation device generates a motion-corrected reconstruction of the scanned region based on the motion-corrected patch reconstructions and on the patch weights. Finally, the flow ends in block B1660.

Figure 17:
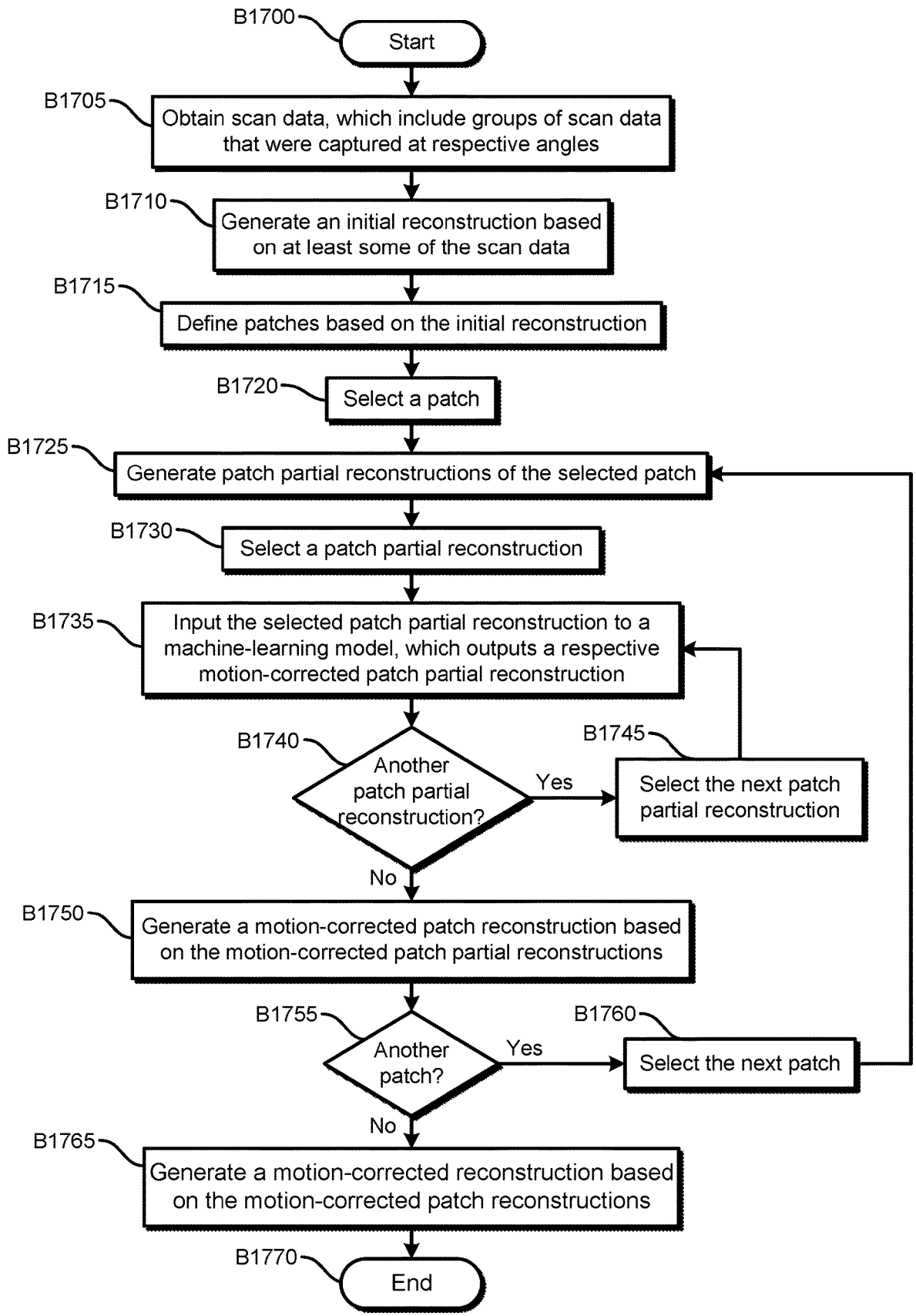
FIG. 17 illustrates an example embodiment of an operational flow for generating a motion-corrected reconstruction.

FIG. 17 illustrates an example embodiment of an operational flow for generating a motion-corrected reconstruction of a scanned region. The flow begins in block B1700 and moves to block B1705, where an image-generation device obtains scan data, which include groups of scan data that were captured at respective angles. Next, in block B1710, the image-generation device generates an initial reconstruction of a scanned region based on at least some of the groups of scan data. The flow then proceeds to block B1715, where the image-generation device defines patches in the scanned region based on the initial reconstruction. Next, in block B1720, the image-generation device selects a patch.

The flow then advances to block B1725, where the image-generation device generates two or more patch partial reconstructions of the selected patch based on the scan data in the groups of scan data that correspond to the selected patch. The flow then proceeds to block B1730, where the image-generation device selects a patch partial reconstruction. Then, in block B1735, the image-generation device inputs the selected patch partial reconstruction into a machine-learning model, which outputs a respective motion-corrected patch partial reconstruction. The flow then proceeds to block B1740.

In block B1740, the image-generation device determines if there is a patch partial reconstruction for which block B1735 has not been performed. If the image-generation device determines that there is a patch partial reconstruction for which block B1735 has not been performed (B1740=Yes), then the flow moves to block B1745, where the image-generation device selects the next patch partial reconstruction, and the flow returns to block B1735. If the image-generation device determines that there is not a patch partial reconstruction for which block B1735 has not been performed (B1740=No), then the flow advances to block B1750.

In block B1750, the image-generation device generates a motion-corrected patch reconstruction based on the motion-corrected patch partial reconstructions.

The flow then moves to block B1755, where the image-generation device determines whether there is at least one patch for which blocks B1725-B1750 have not been performed. If the image-generation device determines that there is at least one patch for which blocks B1725-B1750 have not been performed (B1755=Yes), then the flow proceeds to block B1760, where the image-generation device selects the next patch. The flow then returns to block B1725. If the image-generation device determines that there is no patch for which blocks B1725-B1750 have not been performed (B1755=No), then the flow proceeds to block B1765.

In block B1765, the image-generation device generates a motion-corrected reconstruction of the scanned region based on the motion-corrected patch reconstructions. Finally, the flow ends in block B1770.

Figure 18:
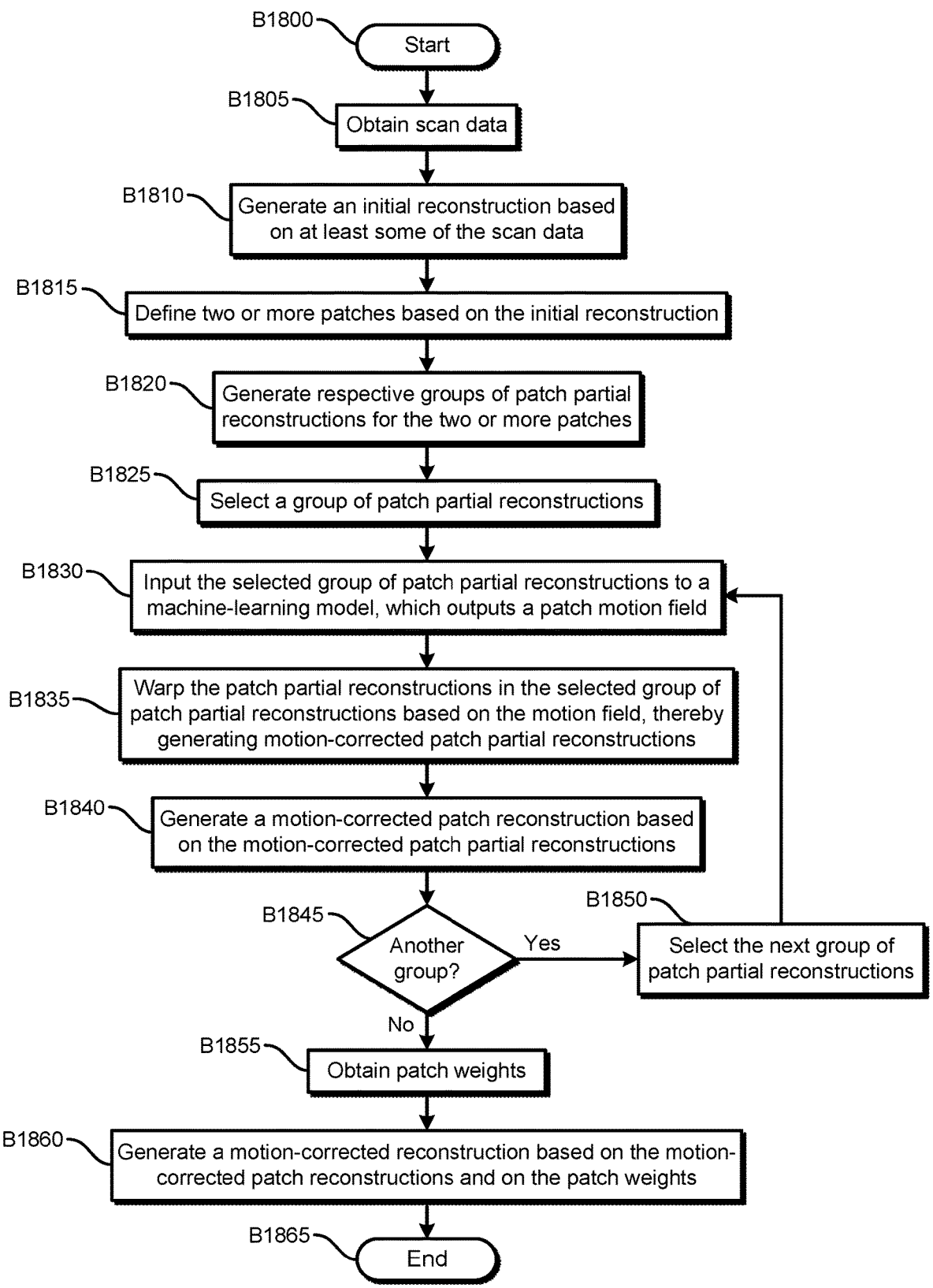
FIG. 18 illustrates an example embodiment of an operational flow for generating a motion-corrected reconstruction.

FIG. 18 illustrates an example embodiment of an operational flow for generating a motion-corrected reconstruction of a scanned region. The flow starts in block B1800 and moves to block B1805, where an image-generation device obtains scan data, which include groups of scan data that were captured at respective angles. Next, in block B1810, the image-generation device generates an initial reconstruction of a scanned region based on at least some of the groups of scan data. The flow then proceeds to block B1815, where the image-generation device defines two or more patches in the scanned region based on the initial reconstruction.

Then, in block B1820, the image-generation device generates respective groups of patch partial reconstructions for the two or more patches. The flow then moves to block B1825, where the image-generation device selects a group of patch partial reconstructions.

Next, in block B1830, the image-generation device inputs the selected group of patch partial reconstructions to a machine-learning model, which outputs a patch motion field. The flow advances to block B1835, where the image-generation device warps the patch partial reconstructions in the selected group of patch partial reconstructions based on the motion field, thereby generating motion-corrected patch partial reconstructions. Then, in block B1840, the image-generation device generates a motion-corrected patch reconstruction based on the motion-corrected patch partial reconstructions.

The flow then advances to block B1845, where the image-generation device determines whether there is another group of patch partial reconstructions on which blocks B1830-B1840 have not been performed. If the image-generation device determines that there is another group of patch partial reconstructions on which blocks B1830-B1840 have not been performed (B1845=Yes), then the flow proceeds to block B1850, where the image-generation device selects the next group of patch partial reconstructions. The flow then returns to block B1830. If the image-generation device determines that there is not another group of patch partial reconstructions on which blocks B1830-B1840 have not been performed (B1845=No), then the flow advances to block B1855.

In block B1855, the image-generation device obtains respective patch weights for the two or more patches. Then, in block B1860, the image-generation device generates a motion-corrected reconstruction of the scanned region based on the motion-corrected patch reconstructions and on the patch weights. The flow then ends in block B1865.

Figure 19:
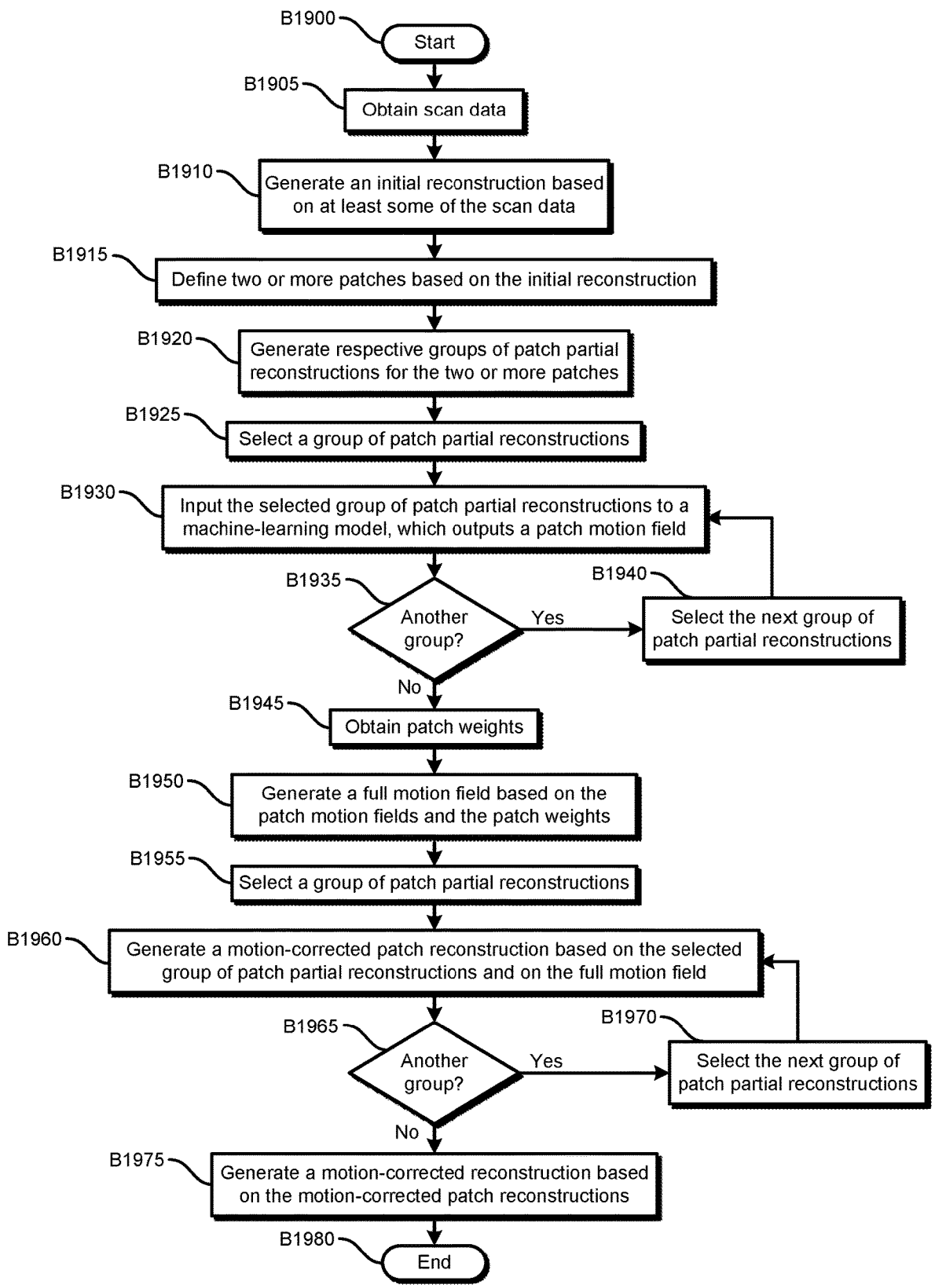
FIG. 19 illustrates an example embodiment of an operational flow for generating a motion-corrected reconstruction.

FIG. 19 illustrates an example embodiment of an operational flow for generating a motion-corrected reconstruction of a scanned region. The flow starts in block B1900 and then proceeds to block B1905, where an image-generation device obtains scan data, which include groups of scan data that were captured at respective angles. Next, in block B1910, the image-generation device generates an initial reconstruction of a scanned region based on at least some of the groups of scan data. The flow then proceeds to block B1915, where the image-generation device defines two or more patches in the scanned region based on the initial reconstruction.

The flow then advances to block B1920, where an image-generation device generates respective groups of patch partial reconstructions for the two or more patches. Next, in block B1925, the image-generation device selects a group of patch partial reconstructions. Then, in block B1930, the image-generation device inputs the selected group of patch partial reconstructions to a machine-learning model, which outputs a patch motion field for the patch.

The flow then moves to block B1935, where the image-generation device determines whether there is a group of patch partial reconstructions for which block B1930 has not been performed. If the image-generation device determines that there is a group of patch partial reconstructions for which block B1930 has not been performed (B1935=Yes), then the flow moves to block B1940, where the image-generation device selects the next group of patch partial reconstructions, and the flow then returns to block B1930. If the image-generation device determines that there is not a group of patch partial reconstructions for which block B1930 has not been performed (B1935=No), then the flow proceeds to block B1945.

In block B1945, the image-generation device obtains patch weights. Next, in block B1950, the image-generation device generates a full motion field based on the patch motion fields and on the patch weights.

The flow then advances to block B1955, where the image-generation device selects a group of patch partial reconstructions. Next, in block B1960, the image-generation device generates a motion-corrected patch reconstruction based on the selected group of patch partial reconstructions and on the full motion field. The flow then moves to block B1965, where the image-generation device determines whether there is a group of patch partial reconstructions (or a patch) for which block B1960 has not been performed. If the image-generation device determines that there is a group of patch partial reconstructions (or a patch) for which block B1960 has not been performed (B1965=Yes), then the flow moves to block B1970, where the image-generation device selects the next group of patch partial reconstructions, and the flow then returns to block B1960. If the image-generation device determines that there is not a group of patch partial reconstructions (or a patch) for which block B1960 has not been performed (B1965=No), then the flow proceeds to block B1975.

In block B1975, the image-generation device generates a motion-corrected reconstruction of the scanned region based on the motion-corrected patch reconstructions. The flow then ends in block B1980.

Figure 20:
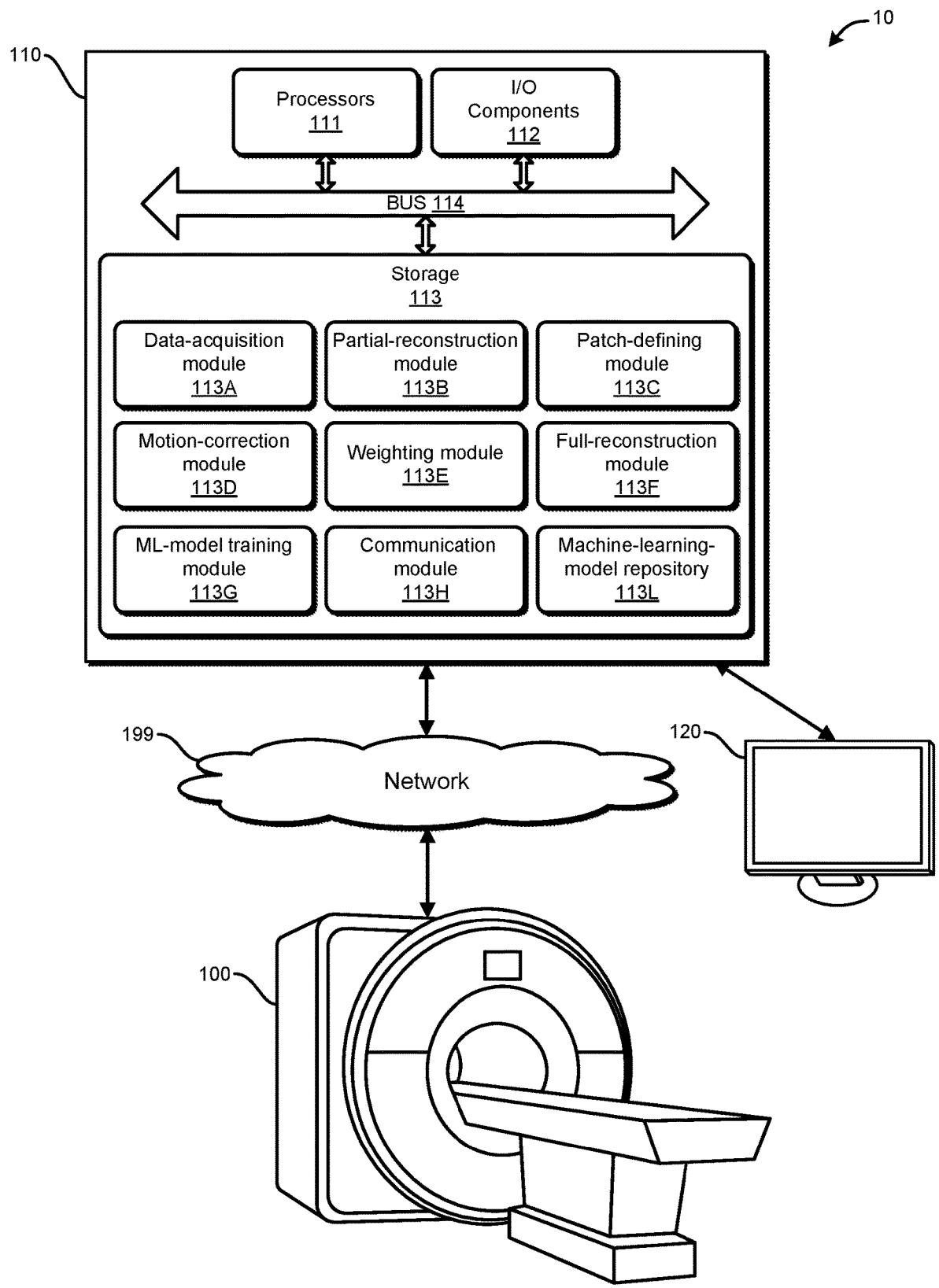
FIG. 20 illustrates an example embodiment of a medical-imaging system.

FIG. 20 illustrates an example embodiment of a medical-imaging system. The system 10 includes a scanning device 100; an image-generation device 110, which is a specially-configured computing device; and a display device 120. In this embodiment, the image-generation device 110 and the scanning device 100 communicate via one or more networks 199, which may include a wired network, a wireless network, a LAN, a WAN, a MAN, and a PAN. Also, in some embodiments the devices communicate via other wired or wireless channels.

The image-generation device 110 includes one or more processors 111, one or more I/O components 112, and storage 113. Also, the hardware components of the image-generation device 110 communicate via one or more buses 114 or other electrical connections. Examples of buses 114 include a universal serial bus (USB), an IEEE 1394 bus, a PCI bus, an Accelerated Graphics Port (AGP) bus, a Serial AT Attachment (SATA) bus, and a Small Computer System Interface (SCSI) bus.

The one or more processors 111 include one or more central processing units (CPUs), which include microprocessors (e.g., a single core microprocessor, a multi-core microprocessor); one or more graphics processing units (GPUs); one or more application-specific integrated circuits (ASICs); one or more field-programmable-gate arrays (FPGAs); one or more digital signal processors (DSPs); or other electronic circuitry (e.g., other integrated circuits). The I/O components 112 include communication components (e.g., a GPU, a network-interface controller) that communicate with the display device 120, the network 199, the scanning device 100, and input or output devices (not illustrated), which may include a keyboard, a mouse, a printing device, a touch screen, a light pen, an optical-storage device, a scanner, a microphone, a drive, and a controller (e.g., a joystick, a control pad).

The storage 113 includes one or more computer-readable storage media. As used herein, a computer-readable storage medium refers to a computer-readable medium that includes an article of manufacture, for example a magnetic disk (e.g., a floppy disk, a hard disk), an optical disc (e.g., a CD, a DVD, a Blu-ray), a magneto-optical disk, magnetic tape, and semiconductor memory (e.g., a non-volatile memory card, flash memory, a solid-state drive, SRAM, DRAM, EPROM, EEPROM). The storage 113, which may include both ROM and RAM, can store computer-readable data or computer-executable instructions. The storage also includes a machine-learning-model repository 113L, which stores machine-learning models.

The image-generation device 110 additionally includes a data-acquisition module 113A, a partial-reconstruction module 113B, a patch-defining module 113C, a motion-correction module 113D, a weighting module 113E, a full-reconstruction module 113F, a machine-learning-model-training (ML-model-training) module 113G, and a communication module 113H. A module includes logic, computer-readable data, or computer-executable instructions. In the embodiment shown in FIG. 20, the modules are implemented in software (e.g., Assembly, C, C++, C#, Java, BASIC, Perl, Visual Basic). However, in some embodiments, the modules are implemented in hardware (e.g., customized circuitry) or, alternatively, a combination of software and hardware. When the modules are implemented, at least in part, in software, then the software can be stored in the storage 113. Also, in some embodiments, the image-generation device 110 includes additional or fewer modules, the modules are combined into fewer modules, or the modules are divided into more modules.

The data-acquisition module 113A includes instructions that cause the image-generation device 110 to obtain scan data from the scanning device 100. For example, some embodiments of the data-acquisition module 113A include instructions that cause the image-generation device 110 to perform at least some of the operations that are described in block B310 in FIG. 3, in block B505 in FIG. 5, in block B705 in FIG. 7, in block B905 in FIG. 9, in block B1410 in FIG. 14, in block B1505 in FIG. 15, in block B1605 in FIG. 16, in block B1705 in FIG. 17, in block B1805 in FIG. 18, and in block B1905 in FIG. 19.

The partial-reconstruction module 113B includes instructions that cause the image-generation device 110 to generate partial reconstructions, such as patch partial reconstructions. For example, some embodiments of the partial-reconstruction module 113B include instructions that cause the image-generation device 110 to perform at least some of the operations that are described in block B320 in FIG. 3, in block B525 in FIG. 5, in block B710 in FIG. 7, in block B925 in FIG. 9, in block B1105 in FIG. 11, in block B1305 in FIG. 13, in block B1420 in FIG. 14, in block B1510 in FIG. 15, in block B1625 in FIG. 16, in block B1725 in FIG. 17, in block B1820 in FIG. 18, and in block B1920 in FIG. 19.

The patch-defining module 113C includes instructions that cause the image-generation device 110 to generate an initial reconstruction of a scanned region and define one or more patches in the scanned region based on the initial reconstruction. For example, some embodiments of the patch-defining module 113C include instructions that cause the image-generation device 110 to perform at least some of the operations that are described in blocks B510-B515 in FIG. 5, in blocks B910-B915 in FIG. 9, in block B1105 in FIG. 11, in block B1305 in FIG. 13, in blocks B1610-B1615 in FIG. 16, in blocks B1710-B1715 in FIG. 17, in blocks B1810-B1815 in FIG. 18, and in blocks B1910-B1915 in FIG. 19.

The motion-correction module 113D includes instructions that cause the image-generation device 110 to use one or more machine-learning models to generate motion-corrected reconstructions, motion-corrected patch reconstructions, or motion-corrected patch partial reconstructions. For example, some embodiments of the motion-correction module 113D include instructions that cause the image-generation device 110 to perform at least some of the operations that are described in block B330 in FIG. 3, in block B530 in FIG. 5, in blocks B720-B730 in FIG. 7, in blocks B935-B945 in FIG. 9, in blocks B1105-B1135 in FIG. 11, in blocks B1310-B1325 and B1335-B1355 in FIG. 13, in block B1430 in FIG. 14, in blocks B1515-B1535 in FIG. 15, in blocks B1620 and B1630-B1640 in FIG. 16, in blocks B1720 and B1730-B1760 in FIG. 17, in blocks B1825-B1850 in FIG. 18, and in blocks B1925-B1970 in FIG. 19.

The weighting module 113E includes instructions that cause the image-generation device 110 to obtain one or more weights for respective patches. For example, some embodiments of the weighting module 113E include instructions that cause the image-generation device 110 to perform at least some of the operations that are described in block B1140 in FIG. 11, in block B1330 in FIG. 13, in blocks B1645-B1650 in FIG. 16, in block B1855 in FIG. 18, and in block B1945 in FIG. 19.

The full-reconstruction module 113F includes instructions that cause the image-generation device 110 to generate full reconstructions of scanned regions (e.g., motion-corrected reconstructions). For example, the full reconstructions may be generated based on scan data, on motion-corrected partial reconstructions, on motion-corrected patch reconstructions, or on motion-corrected patch partial reconstructions. Also for example, some embodiments of the full-reconstruction module 113F include instructions that cause the image-generation device 110 to perform at least some of the operations that are described in block B735 in FIG. 7, in block B950 in FIG. 9, in block B1145 in FIG. 11, in block B1360 in FIG. 13, in block B1535 in FIG. 15, in block B1655 in FIG. 16, in block B1765 in FIG. 17, in block B1860 in FIG. 18, and in block B1975 in FIG. 19.

The ML-model-training module 113G includes instructions that cause the image-generation device 110 to calculate edge entropies and train (e.g., modify, adjust) machine-learning models based on the edge entropies. For example, some embodiments of the ML-model-training module 113G include instructions that cause the image-generation device 110 to perform at least some of the operations that are described in blocks B340-B350 in FIG. 3, in blocks B535-B540 in FIG. 5, in blocks B740-B745 in FIG. 7, in blocks B955-B960 in FIG. 9, in blocks B1150-B1155 in FIG. 11, and in blocks B1365-B1370 in FIG. 13.

The communication module 113H includes instructions that cause the image-generation device 110 to communicate with other devices, such as the display device 120, the scanning device 100, and other computing devices. For example, some embodiments of the communication module 113H include instructions that cause the image-generation device 110 to perform at least some of the operations that are described in block B1440 in FIG. 14 and in block B1540 in FIG. 15.

The scope of the claims is not limited to the above-described embodiments and includes various modifications and equivalent arrangements.

The invention claimed is:

1. A method comprising:
obtaining scan data that were generated by scanning a scanned region,
wherein the scan data include groups of scan data,
wherein each group, of the groups of scan data, was captured at a respective angle, and
wherein each group's respective angle is different from every other group's respective angle;
performing a reconstruction process on a first subset of the groups of scan data, thereby generating a first partial reconstruction of at least part of the scanned region;
performing a reconstruction process on a second subset of the groups of scan data, thereby generating a second partial reconstruction of the at least part of the scanned region, wherein the first subset is different from the second subset;
inputting the first partial reconstruction and the second partial reconstruction into a machine-learning model, which generates one or more motion-compensated reconstructions of the at least part of the scanned region based at least on the first partial reconstruction and the second partial reconstruction;
calculating a respective edge entropy of each of the one or more motion-compensated reconstructions of the at least part of the scanned region; and
adjusting the machine-learning model based on the respective edge entropy of each of the one or more motion-compensated reconstructions.

2. The method of claim 1, wherein the machine-learning model includes a neural network.

3. The method of claim 2, wherein edge entropy of motion-compensated reconstructions is a loss function of the neural network.

4. The method of claim 1, wherein the one or more motion-compensated reconstructions include a plurality of motion-compensated reconstructions, and
wherein the machine-learning model is further configured to calculate a respective motion of each pixel in the plurality of motion-compensated reconstructions based on the plurality of motion-compensated reconstructions.

5. The method of claim 4, wherein the machine-learning model is further configured to generate a smoothed motion-compensated reconstruction of the scanned region based on the respective motion of each pixel and on the plurality of motion-compensated reconstructions.

6. The method of claim 5, wherein generating the smoothed motion-compensated reconstruction includes warping the plurality of motion-compensated reconstructions.

7. The method of claim 5, wherein the respective edge entropies are calculated based on the smoothed motion-compensated reconstruction of the scanned region.

8. The method of claim 1, wherein the first subset and the second subset do not have any groups in common.

9. The method of claim 1, wherein the first subset and the second subset have at least one group in common.

10. The method of claim 1, further comprising:
performing a reconstruction process on a third subset of the groups of scan data, thereby generating a third partial reconstruction of the at least part of the scanned region;
performing a reconstruction process on a fourth subset of the groups of scan data, thereby generating a fourth partial reconstruction of the at least part of the scanned region,
wherein the first subset, the second subset, the third subset, and the fourth subset are all different from each other; and
inputting the third partial reconstruction and the fourth partial reconstruction into the machine-learning model, which generates the one or more motion-compensated reconstructions of the at least part of the scanned region further based at least on the third partial reconstruction and the fourth partial reconstruction.

11. A system comprising:
one or more processors; and
one or more computer-readable storage media in communication with the one or more processors, wherein the one or more processors and the one or more computer-readable storage media cooperate to perform operations including:
obtaining scan data that were generated by scanning a scanned region,
wherein the scan data include groups of scan data,
wherein each group, of the groups of scan data, was captured at a respective angle, and
wherein each group's respective angle is different from every other group's respective angle;
performing a reconstruction process on a first subset of the groups of scan data, thereby generating a first partial reconstruction of at least part of the scanned region;
performing a reconstruction process on a second subset of the groups of scan data, thereby generating a second partial reconstruction of the at least part of the scanned region, wherein the first subset is different from the second subset;
generating a motion-corrected reconstruction of the at least part of the scanned region, wherein generating the motion-correct reconstruction includes inputting the first partial reconstruction and the second partial reconstruction into a machine-learning model.

12. The system of claim 11, wherein the machine-learning model outputs the motion-corrected reconstruction of the at least part of the scanned region.

13. The system of claim 11, wherein the operations further include:
calculating an edge entropy of the motion-corrected reconstruction of the at least part of the scanned region; and
modifying the machine-learning model based on the edge entropy.

14. The system of claim 11, wherein the machine-learning model outputs a respective motion-corrected partial reconstruction of each of the partial reconstructions, and
wherein the motion-corrected reconstruction is generated from the motion-corrected partial reconstructions.

15. The system of claim 11, wherein the at least part of the scanned region includes part of an object of interest.

16. The system of claim 15, wherein the object of interest is a cardiac vessel.

17. One or more computer-readable storage media storing instructions that, when executed by one or more computing devices, cause the one or more computing devices to perform operations comprising:
obtaining scan data that were generated by scanning a scanned region,
wherein the scan data include groups of scan data,
wherein each group, of the groups of scan data, was captured at a respective angle, and
wherein each group's respective angle is different from every other group's respective angle;
performing a reconstruction process on a first subset of the groups of scan data, thereby generating a first partial reconstruction of at least part of the scanned region;
performing a reconstruction process on a second subset of the groups of scan data, thereby generating a second partial reconstruction of the at least part of the scanned region, wherein the first subset is different from the second subset;
inputting the first partial reconstruction and the second partial reconstruction into a machine-learning model, which generates one or more motion-compensated reconstructions of the at least part of the scanned region based at least on the first partial reconstruction and the second partial reconstruction;
calculating a respective edge entropy of each of the one or more motion-compensated reconstructions of the at least part of the scanned region; and
adjusting the machine-learning model based on the respective edge entropy of each of the one or more motion-compensated reconstructions.

18. The one or more computer-readable storage media of claim 17, wherein the scan data were obtained by computed-tomography scanning.

19. The one or more computer-readable storage media of claim 17, wherein the machine-learning model is a neural network.

20. The one or more computer-readable storage media of claim 19, wherein edge entropy of motion-compensated reconstructions is a loss function of the neural network.

* * * * *